(12) United States Patent
Wu et al.

(10) Patent No.: US 8,198,029 B2
(45) Date of Patent: Jun. 12, 2012

(54) 3'-OH UNBLOCKED NUCLEOTIDES AND NUCLEOSIDES BASE MODIFIED WITH NON-CLEAVABLE, TERMINATING GROUPS AND METHODS FOR THEIR USE IN DNA SEQUENCING

(75) Inventors: Weidong Wu, Houston, TX (US); Vladislav A. Litosh, Cypress, TX (US); Brian P. Stupi, Houston, TX (US); Michael L. Metzker, Houston, TX (US)

(73) Assignee: Lasergen, Inc, Houston, TX (US)

( * ) Notice: Subject to any disclaimer, the term of this patent is extended or adjusted under 35 U.S.C. 154(b) by 0 days.

(21) Appl. No.: 12/986,810

(22) Filed: Jan. 7, 2011

(65) Prior Publication Data
US 2011/0200988 A1    Aug. 18, 2011

Related U.S. Application Data

(62) Division of application No. 11/567,193, filed on Dec. 5, 2006, now Pat. No. 7,893,227.

(51) Int. Cl.
*C12Q 1/70* (2006.01)
*C12P 19/34* (2006.01)
(52) U.S. Cl. ........................ 435/6.12; 435/91.1; 435/91.5
(58) Field of Classification Search .................. None
See application file for complete search history.

(56) References Cited

U.S. PATENT DOCUMENTS

| | | | |
|---|---|---|---|
| 4,318,846 A | 3/1982 | Khanna et al. | 530/391.5 |
| 4,439,356 A | 3/1984 | Khanna et al. | 530/350 |
| 4,657,897 A | 4/1987 | Bristol et al. | 514/47 |
| 4,704,381 A | 11/1987 | Schaumann et al. | 514/46 |
| 5,151,507 A | 9/1992 | Hobbs, Jr. et al. | 536/26.7 |
| 5,188,934 A | 2/1993 | Menchen et al. | 435/6 |
| 5,614,386 A | 3/1997 | Metzker et al. | 435/91.1 |
| 5,684,142 A | 11/1997 | Mishra et al. | 536/22.1 |
| 5,728,529 A | 3/1998 | Metzker et al. | 435/6 |
| 5,763,594 A | 6/1998 | Hiatt et al. | 536/25.3 |
| 5,770,367 A | 6/1998 | Southern et al. | 435/6 |
| 5,773,423 A | 6/1998 | Jacobson et al. | 514/45 |
| 5,808,045 A | 9/1998 | Hiatt et al. | 536/26.26 |
| 5,861,287 A | 1/1999 | Metzker et al. | 435/91.1 |
| 5,872,244 A | 2/1999 | Hiatt et al. | 536/26.26 |
| 5,994,063 A | 11/1999 | Metzker et al. | 435/6 |
| 6,214,987 B1 | 4/2001 | Hiatt et al. | 536/26.26 |
| 6,579,704 B2 | 6/2003 | Short | 435/91.1 |
| 6,664,079 B2 | 12/2003 | Ju et al. | 435/91.91 |
| 6,762,048 B2 | 7/2004 | Williams | 435/287.1 |
| 6,818,395 B1 | 11/2004 | Quake et al. | 435/6 |
| 6,833,246 B2 | 12/2004 | Balasubramanian | 435/6 |
| 6,869,764 B2 | 3/2005 | Williams et al. | 435/6 |
| 6,995,841 B2 | 2/2006 | Scott et al. | 356/318 |
| 7,125,660 B2 | 10/2006 | Stanton et al. | 435/4 |
| 7,355,036 B2 | 4/2008 | Guimil et al. | 536/25.3 |
| 7,476,734 B2 | 1/2009 | Liu | 536/26.21 |
| 2003/0180769 A1 | 9/2003 | Metzker | 435/6 |
| 2004/0014096 A1 | 1/2004 | Anderson et al. | 435/6 |
| 2005/0048601 A1 | 3/2005 | Dellinger et al. | 435/68.1 |
| 2005/0049407 A1 | 3/2005 | Dellinger et al. | 536/17.4 |
| 2005/0049411 A1 | 3/2005 | Dellinger et al. | 536/25.3 |
| 2008/0131952 A1 | 6/2008 | Wu et al. | 435/6 |
| 2008/0132692 A1 | 6/2008 | Wu et al. | 435/6 |
| 2009/0081686 A1 | 3/2009 | Wu et al. | 536/25.3 |

FOREIGN PATENT DOCUMENTS

| | | |
|---|---|---|
| EP | 0 272 007 | 6/1988 |
| EP | 0 866 071 | 9/1998 |
| WO | WO 91/05060 | 4/1991 |
| WO | WO 97/00967 | 1/1997 |
| WO | WO 03/021212 | 3/2003 |
| WO | WO 03/087302 | 10/2003 |
| WO | WO 2004/018497 | 3/2004 |
| WO | WO 2004/058791 | 7/2004 |

OTHER PUBLICATIONS

Michael L. Metzker, Sequencing technologies—the next generation, Nature, Jan. 2010|vol. 11, pp. 31-46.*

Wu et al., Termination of DNA synthesis by N6-alkylated, not 3'-O-alkylated, photocleavable 2'-deoxyadenosine triphosphates, Published online Sep. 18, 2007, Nucleic Acids Research, 2007, vol. 35, No. 19 pp. 6339-6349.*

Litosh et al., Improved nucleotide selectivity and termination of 30-OH unblocked reversible terminators by molecular tuning of 2-nitrobenzyl alkylated HOMedU triphosphates, Published online Jan. 11, 2011, Nucleic Acids Research, 2011, vol. 39, No. 6 e39, pp. 1-13.*

Adzamli et al., "Development of phosphonate derivatives of gadolinium chelates for NMR imaging of calcified soft tissues," *J. Med. Chem.*, 32(1):139-144, 1989.

Agbanyo et al., "5'-S-(2-aminoethyl)-N6-(4-nitrobenzyl)-5'-thioadenosine (SAENTA), a novel ligand with high affinity for polypeptides associated with nucleoside transport. Partial purification of the nitrobenzylthioinosine-binding protein of pig erythrocytes by affinity chromatography," *Biochem. J.*, 270:605-614, 1990.

Bartholomew and Broom, "One-step chemical synthesis of ribonucleosides bearing a photolabile ether protecting group," *J. Chem. Soc. Chem. Commun.*, 38, 1975.

Berlier et al. "Quantitative comparison of long-wavelength alexa fluor dyes to cy dyes: fluorescence of the dyes and their bioconjugates," *The Journal of Histochemistry & Cytochemistry*, 51(12):1699-1712, 2003.

(Continued)

*Primary Examiner* — Mark Staples
(74) *Attorney, Agent, or Firm* — Fulbright & Jaworski L.L.P.

(57) ABSTRACT

Provided are novel nucleotides, nucleoside, and their derivatives described herein, that can be used in DNA sequencing technology and other types of DNA analysis. In one embodiment, the nucleotide or nucleoside with an unprotected 3'-OH group is derivatized at the nucleobase to include a fluorescent dye attached via a linker to a non-cleavable terminating group. The non-cleavable-fluorescent group is designed to terminate DNA synthesis so that DNA oligomers can be sequenced efficiently in a parallel format. These reagents and methods will lead to more accurate identification of polymorphisms and other valuable genetic information.

29 Claims, No Drawings

OTHER PUBLICATIONS

Bodepudi et al., "Synthesis of 2'-deoxy-7,8-dihydro-8-oxoguanosine and 2'-deoxy-7,8-dihydro-8-oxoadenosine and their incorporation into oligomeric DNA," *Chem. Res. Toxicol.*, 5:608-617, 1992.

Brandis, "Dye structure affects *Taq* DNA polymerase terminator selectivity," *Nucleic Acids Research*, 27(8):1912-1918, 1999.

Bressi et al.,"Adenosine analogues as inhibitors of *Trypanosoma brucei* phosphoglycerate kinase: Elucidation of a novel binding mode for a 2-amino-$N^6$ substituted andenosine," *J. Med. Chem.*, 43;4135-4250, 2000.

Chaulk and MacMillan, "Caged RNA: photo-control of a ribozyme reaction," *Nucleic Acids Res.*, 26:3173-3178, 1998.

Chaves des Neves and Pais, "Identification of a spathe regreening factor in *zantedeschia aethiopicia,*" *Biochemical and Biophysical Research Communications*, 95(4):1387-1392, 1980.

Cho et al., "$^{15}$N nuclear magnetic resonance studies on the tautomerism of 8-hydroxy-2'-deoxyguanosine, 8-hydroxyguanosine, and other C8-substituted guanine nucleosides," *Chem. Res. Toxicol.*, 3:445-452, 1990.

Cho et al., "Correlation between NMR spectral parameters of nucleosides and its implication to the conformation about the glycosyl bond," *Biochemical and Biophysical Research Communications*, 180(1):273-278, 1991.

Corrigenda in: Welch et al., "Synthesis of nucleosides designed for combinatorial DNA sequencing," *Chem. Eur. J.*, 11:7145, 2005.

Dewey et al., "New uridine derivatives for systematic evolution of RNA ligands by exponential enrichment," *J. Am. Chem. Soc.*, 117:8474-8475, 1995.

Dressman et al., "Transforming single DNA molecules into fluorescent magnetic particles for detection and enumeration of genetic variations," *Proc. Natl. Acad. Sci. USA*, 100:8817-8822, 2003.

Dutta et al., "Synthesis and biological activities of some N6-(nitro- and -aminobenzyl)adenosines," *Journal of Medicinal Chemistry*, 18(8):780-783, 1975.

Erratum in: Welch and Burgess, "Synthesis of fluorescent, photolabile 3'-O-protected nucleoside triphosphates for the base addition sequencing scheme," *Nucleosides, Nucleotides, and Nucleic Acids*, 25:119, 2006.

Friest et al., "Valyl-tRNA, Isoleucyl-tRNA and Tyrosyl-tRNA synthetase from Baker's Yeast," *Eur. J. Biochem.*, 66:493-497, 1976.

Gao et al., "Structural determinants of A3 adenosine receptor activation: Nucleoside ligands at the agonist/antagonist boundary," *J. Med. Chem.*, 45:4471-4484, 2002.

Gardner and Jack, "Acyclic and dideoxy terminator preferences denote divergent sugar recognition by archaaeon and *Taq* DNA polymerases," *Nucleic Acids Research*, 30(2):605-613, 2002.

Gardner and Jack, "Determinants of nucleotide sugar recognition in an archaeon DNA polymerase," *Nucleic Acids Research*, 27(12):2545-2553, 1999.

Gebeyehu et al., "Novel biotinylated nucleotide—analogs for labeling and colorimetric detection of DNA," *Nucleic Acids Research*, 15(11):4513-4534, 1987.

Gibbs, "Identification of mutations leading to the Lesch-Nyhan syndrome by automated direct DNA sequencing of in vitro amplified cDNA," *Proc. Natl. Acad. Sci. USA*, 86:1919-1923, 1989.

Golisade et al., "Anti-malarial activity of $N^6$-substituted Adenosine derivatives. Part I.," *Bioorganic & Medicinal Chemistry*, 10:769-777, 2002.

Gommers-Ampt and Borst, "Hypermodified bases in DNA," *FASEB J.*, 9(11):1034-1042, 1995.

Hampton et al., "Species- or isozyme-specific enzyme inhibitors. 4. Design of a two-site inhibitor of adenylate kinase with isozyme selectivity," *J. Med. Chem.*, 25:638-644, 1982.

Harris et al., "Single-molecule DNA sequencing of a viral genome," *Science*, 320:106-109, 2008.

Hashizume et al., "Synthesis and cytokinin activity of alpha-anomeric $N^6$-benzyladenosine," *Agric. Biol. Chem.*, 49(1):225-227, 1985.

Henderson et al., "4,4'-Dimethoxytrityl and 4,4',4"-trimethoxytrityl as protecting tropus for amino functions; selectivity for primary amino groups and application in $^{15}$N-labeling," *J. Chem. Soc. Perkin Trans.*, 1:3407-3413, 1997.

Hermanns et al., "Synthesis of 8-[18O]hydroxy-2'-deoxyguanosine," *Journal of Labelled Compounds and Radiopharmaceuticals*, 36(2):191-197, 1993.

Hobarnter and Silverman, "Modulation of RNA tertiary folding by incorporation of caged nucleotides," *Angew. Chem. Int. Ed.*, 44:7305-7309, 2005.

Holmes and Robins, "Purine nucleosides. IX. The synthesis of 9-beta-D-Ribofuranysyl uric acid and other related 8-substituted purine ribonucleosides," *Journal of the American Chemical Society*, 87:8:1772-176, 1965.

Honda et al., "New type of prefabricated fully protected ribonucleotide monomer unites as useful synthetic intermediates in rapid oligoribonucleotide synthesis," *Chemistry Letters*, pp. 15-18, 1982.

International Human Genome Sequencing Consortium., "Initial sequencing and analysis of the human genome," *Nature*, 409:860-921, 2001.

International Preliminary Report on Patentability, issued in International Patent Application No. PCT/US2007/086559, mail date Jun. 18, 2009.

International Search Report issued in International Application No. PCT/US07/86559, mailed Aug. 21, 2008.

Jacobson et al., "Methancarba analogues of purine nucleosides as potent and selective adenosine receptor agonists," *J. Med. Chem.*, 43:2196-2203, 2000.

Ju et al., "Fluorescence energy transfer dye-labeled primers for DNA sequencing and analysis," *Proc. Natl. Acad. Sci USA*, 92:4347-4351, 1995.

Ju et al., "Four-color DNA sequencing by synthesis using cleavable fluorescent nucleotide reversible terminators," *Proc. Natl. Acad. Sci. USA*, 103:19635-40, 2006.

Kahl et al., "Introducing structural diversity in oligonucleotides via photolabile, concertible C5-substituted nucleotides," *K. Am. Chem. Soc.*, 121(4):597-604, 1999.

Kim et al., "2-Substitution of N6-benzyladenosine-5'-uronamides enhances selectivity for A3 adenosine receptors," *J. Med. Chem.*, 37:3614-3621, 1994.

Kobayashi et al., "A microfluidic device for conducting gas-liquid-solid hydrogenation reactions," *Science*, 304:1305-1308, 2004.

Kong et al., "Characterization of a DNA polymerase from the hyperthermophile archaea *thermococcus litoralis*," *The Journal of Biological Chemistry*, 268(3):I965-1975, 1993.

Kornher and Livak, "Mutation detection using nucleotide analogs that alter electrophoretic mobility," *Nucleic Acids Research*, 17(19):7779-7784, 1989.

Kulikowski et al., "Structure-activity relationships and conformational features of antiherpetic pyrimidine and purine analogues. A review," *Pharmacy World & Science*, 16(2):127-138, 1994.

Lee et al., "New energy transfer dyes for DNA sequencing," *Nucleic Acids Research*, 25(14):2816-2822, 1997.

Levy et al., "The diploid genome sequence of an individual human," *PLoS Biol.*, 5:e254, 2007.

Lewis et al., "Color-blind fluorescence detection for four-color DNA sequencing," *PNAS*, 102(15):5346-5351, 2005.

Li et al., "A photocleavable fluorescent nucleotide for DNA sequencing and analysis," *PNAS*, 100(2):414-419, 2003.

Lin et al., "8-substituted guanosine and 2'-Deoxyguanosine derivatives as potential inducers of the differentiation of friend erythroleukemia cells," *J. Med. Chem.*, 28:1194-1198, 1985.

Liu et al., "A molecular gate which controls unnatural ATP analogue recognition by the tyrosine kinase v-Src," *Bioorganic & Medicinal Chemistry*, 6:1219-1226, 1998.

Malecki et al., "Mutations in NEUROD1 are associated with the development of type 2 diabetes mellitus," *Nature Genetics*, 23:323-328, 1999.

McMinn et al., Novel solid phase synthesis supports for the preparation of oligonucleotides containing 3'- Alykl Amines, *Tetrahedron*, 52:3827-3840, 1996.

Metzker et al.,"Electrophoretically uniform fluorescent dyes for automated DNA sequencing," *Science*, 271:1420-1422, 1996.

Metzker et al., "Elimination of residual natural nucleotides from 3'-O-modified-dNTP syntheses by enzymatic mop-up," *BioTechniques*, 25:814-817, 1998.

Metzker et al., "Emerging technologies in DNA sequencing," *Genome Research*, 15:1767-1776, 2005.

Metzker et al., "Termination of DNA synthesis by novel 3'-modified-deoxyribonucleoside 5'-triphosphates," *Nucleic Acids Res.*, 22:4259-4267, 1994.

Molecular Probes™ invitrogen detection technologies, "Alexa Fluor® Dyes—Simply the Best and Brightest, Fluorescent dyes and conjugates," 2005.

Moore and Koreeda, "Application of the change in partition coefficient with pH to the structure determination of alkyl substituted guanosines," *Biochemical and Biophysical Research Communications*, 73(2):459-464, 1976.

Mounetou et al., "O6-(alkyl/aralkyl)guanosine and 2'-deoxyguanosine derivatives: synthesis and ability to enhance chloroethylnitrosourea antitumor action," *J. Med. Chem.*, 40:2902-2909, 1997.

Mounteou et al., "Synthesis of three no-carrier-added $O^6$-4-[$^{125}$I] iodobenzylguanosine derivatives, new reagents for the assay of O6-alkylguanine-DNA alkyltransferase activity," *Journal of Labelled Compounds and Radiopharmaceuticals*, 36(12):1216-1225, 1995.

Nampalli et al., "Efficient synthesis of 8-Oxo-dGTP: A mutagnic nucleotide," *Bioorganic & Medicinal Chemistry Letters*, 10:1677-1679, 2000.

Office Action issued in U.S. Appl. No. 11/567,189, mailed Dec. 9, 2008.

Office Action issued in U.S. Appl. No. 11/567,189, mailed Jun. 24, 2009.

Office Action issued in U.S. Appl. No. 11/567,189, mailed Sep. 25, 2008.

Office Action issued in U.S. Appl. No. 12/268,876, mailed Jun. 25, 2009.

Office Action issued in U.S. Appl. No. 12/268,876, mailed Mar. 5, 2009.

Office Communication, issued in U.S. Appl. No. 11/567,193, dated Jul. 14, 2010.

Office Communication, issued in U.S. Appl. No. 11/567,193, dated Jun. 15, 2010.

Office Communication, issued in U.S. Appl. No. 11/567,189, dated Apr. 15, 2010.

Office Communication, issued in U.S. Appl. No. 12/268,876, dated Jul. 12, 2010.

Office Communication, issued in U.S. Appl. No. 12/268,876, dated Jun. 17, 2010.

Office Communication, issued in U.S. Appl. No. 11/567,193, dated Mar. 26, 2010.

Office Communication, issued in U.S. Appl. No. 11/567,193, dated Jun. 22, 2009.

Office Communication, issued in U.S. Appl. No. 11/567,193, dated Nov. 24, 2008.

Office Communication, issued in U.S. Appl. No. 11/567,193, dated Sep. 26, 2008.

Office Communication, issued in U.S. Appl. No. 12/483,080, dated Feb. 15, 2011.

Ohtsuka et al., "Studies on transfer ribonucleic acids and related compounds. IX. Ribooligonucleotide synthesis using a photosensitive o-nitrobenzyl protection at the 2'-hydroxyl group," *Nucleic Acids Res.*, 1:1351-1357, 1974.

Panchuk-Voloshina et al., "Alexa dyes, a series of new fluorescent dyes that yield exceptionally bright, photostable conjugates," *The Journal of Histochemistry & Cytochemistry*, 47(9):1179-1188, 1999.

Pease et al., "Light-generated oligonucleotide arrays for rapid DNA sequence analysis," *Proc. Natl. Acad. Sci. USA*, 91:5022-5026, 1994.

Perler et al., "Intervening sequences in an Archaea DNA polymerase gene," *Proc. Natl. Acad. Sci. USA*, 89:5577-5581, 1992.

Perler et al., "Thermostable DNA polymerases," *Adv. Protein Chem.*, 48:377-435, 1996.

Pillai et al., "Photoremovable protecting groups in organic synthesis," *Synthesis*, 1-26, 1980.

Redon et al., "Global variation in copy number in the human genome," *Nature*, 444:444-454, 2006.

Reeve and Fuller, "A novel thermostable polymerase for DNA sequencing," *Nature*, 376:796-797, 1995.

Response to Office Communication submitted in U.S. Appl. No. 11/567,189, filed Mar. 9, 2009.

Response to Office Communication submitted in U.S. Appl. No. 11/567,189, filed Oct. 27, 2008.

Response to Office Communication submitted in U.S. Appl. No. 12/268,876, filed Apr. 6, 2009.

Response to Office Communication, submitted in U.S. Appl. No. 11/567,189, filed Sep. 29, 2009.

Response to Office Communication, submitted in U.S. Appl. No. 11/567,189, filed Dec. 28, 2009.

Response to Office Communication, submitted in U.S. Appl. No. 11/567,189, filed Oct. 27, 2008.

Response to Office Communication, submitted in U.S. Appl. No. 12/268,876, dated Nov. 24, 2009.

Response to Office Communication, submitted in U.S. Appl. No. 11/567,193, dated May 26, 2010.

Response to Office Communication, submitted in U.S. Appl. No. 11/567,193, dated Dec. 22, 2009.

Response to Office Communication, submitted in U.S. Appl. No. 11/567,193, filed Sep. 22, 2009.

Response to Office Communication, submitted in U.S. Appl. No. 11/567,193, filed Feb. 24, 2009.

Response to Office Communication, submitted in U.S. Appl. No. 11/567,193, filed Oct. 27, 2008.

Response to Office Communication, submitted in U.S. Appl. No. 12/268,876, dated Apr. 6, 2010.

Schold et al., "Treatment of human brain tumor xenografts with O6-benzyl-2'-deoxyguanosine and BCNU," *Cancer Research*, 56:2076-2081, 1996.

Sebat et al., "Large-scale copy number polymorphism in the human genome," *Science*, 305:525-528, 2004.

Seio et al., "Synthesis and properties of new nucleotide analogues processing squaramide moieties as new phosphate isosters," *Eur. J. Org. Chem.*, 5163-5170, 2005.

Seo et al., "Four-color DNA sequencing by synthesis on a chip using photocleavable fluorescent nucleotides," *PNAS*, 102(17):5926-5931, 2005.

Seo et al., "Photocleavable fluorescent nucleotides for DNA sequencing on a chip constructed by site-specific coupling chemistry," *PNAS*, 101(15):5488-5493, 2004.

Shankar et al., "O6-3-[125I]iodobenzyl-2'-deoxyguanosine ([125I]IBdG): synthesis and evaluation of its usefulness as an agent for quantification of alkylguanine-DNA alkyltransferase (AGT)," *Bioorganic & Medicinal Chemistry*, 13:3889-3898, 2005.

Shapiro and Shiuey, "Reactions of cytidine with 7-bromomethylbenz[a]anthracene, benzyl bromide, and p-methoxybenzyl bromide. Ratio of Amino to 3 substitution," *J. Org. Chem.*, 41(9): 1597-1600, 1976.

Sierzchala et al., "Solid-phase oligodeoxynucleotide synthesis: A two-step cycle using peroxy anion deprotection," *J. Am. Chem. Soc.*, 125:13427-13441, 2003.

Southworth et al., "Cloning of thermostable DNA polymerases from hyperthermophilic marine *Archaea* with emphasis on *Thermococcus* sp. 9° N-7 and mutations affecting 3'-5' exonuclease activity," *Proc. Natl. Acad. Sci. USA*, 93:5281-5285, 1996.

Stranger et al., "Relative impact of nucleotide and copy number variation on gene expression phenotypes," *Science*, 315:848-853, 2007.

Tabor and Richardson, "A single residue in DNA polymerases of the *Escherichia coli* DNA polymerase I family is critical for distinguishing between deoxy- and dideoxyribonucleotides," *Proc. Natl. Acad. Sci. USA*, 92:6339-6343, 1995.

Terrashima et al., "Substrate specificity of human $O^6$-methylguanine-DNA methyltransferase for $O^6$-benzylguanine derivatives in oligodeoxynucleotides," *Chem. Res. Toxicol.*, 10:1234-1239, 1997.

U.S. Appl. No. 12/483,080, entitled "Nucleotides and nucleosides and methods for their use in DNA sequencing," by Vladislav A. Litosh et al., filed Jun. 11, 2009.

van Tilburg et al., "$N^6$,5'-disubstituted adenosine derivatives as partial agonists for the human adenosine $A_3$ receptor," *J. Med. Chem.*, 42:1393-1400, 1999.

Vander Horn et al., "Thermo Sequenase™ DNA polymerase and *T. acidophilum* pyrophosphatase: new thermo-stable enzymes for DNA sequencing," *BioTechniques*, 22:758-765, 1997.

Welch and Burgess, "Synthesis of fluorescent, photolabile 3'-O-protected nucleoside triphosphates for the base addition sequencing scheme," *Nucleosides & Nucleotides*, 18(2):197201, 1999.

Welch et al., "Synthesis of nucleosides designed for combinatorial DNA sequencing," *Chem. Eur. J.*, 5(3):951-960, 1999.

Wu et al., "Termination of DNA synthesis by $N^6$-alkylated, not 3'-O-alkylated, photocleavable 2'-deoxyadenosine triphosphates," *Nucleic Acids Research*, 35(19):6339-6349, 2007.

Yamashita et al., "Studies on antitumor agents. IX. Synthesis of 3'-O-benzyl-2'-deoxy-5-trifluoromethyluridine," *Chem Pharm. Bull.*, 37(9):2287-2292, 1989.

Yu et al., "Synthesis of 3,7,8-$^{15}N_3$-$N^1$-(beta-D-*erythro*-pentofuranosyl)-5-guanidinohydantoin," *Journal of Labelled Compounds and Radiopharmaceuticals*, 46:1269-1277, 2003.

PCT Invitation to Pay Additional Fees and Partial International Search Report, issued in International application No. PCT/US2009/047071, dated May 11, 2011.

Turcatti et al., "A new class of cleavable fluorescent nucleotides: synthesis and optimization as reversible terminators for DNA sequencing by synthesis," *Nucleic Acids Research*, 36(4):e25, doi:10.1093/nar/gkn021, 13 pages, 2008.

Office Communication, issued in New Zealand Patent Application No. 590265, dated May 6, 2011.

Office Communication, issued in U.S. Appl. No. 12/483,080, dated May 13, 2011.

English translation of Office Communication issued in Russian Patent Application No. 2009121089, dated Mar. 15, 2012.

\* cited by examiner

3'-OH UNBLOCKED NUCLEOTIDES AND NUCLEOSIDES BASE MODIFIED WITH NON-CLEAVABLE, TERMINATING GROUPS AND METHODS FOR THEIR USE IN DNA SEQUENCING

The present application is a divisional of application Ser. No. 11/567,193, filed Dec. 5, 2006, now U.S. Pat. No. 7,893,227, the entire contents of which is incorporated herein by reference in its entirety without disclaimer.

This invention was made with government support under grant number R01 H0003573-01 awarded by the NHGRI (National Human Genome Research Institute), which is one of the institutes of the NIH. The government has certain rights in this invention.

FIELD OF INVENTION

The present invention relates generally to compounds and methods for DNA sequencing and other types of DNA analysis. More particularly, the invention relates to nucleotides and nucleosides labeled with noncleavable groups and methods for their use in DNA sequencing and analysis.

BACKGROUND

Methods for rapidly sequencing DNA have become needed for analyzing diseases and mutations in the population and developing therapies. The most commonly observed form of human sequence variation is single nucleotide polymorphisms (SNPs), which occur in approximately 1-in-300 to 1-in-1000 base pairs of genomic sequence. Building upon the complete sequence of the human genome, efforts are underway to identify the underlying genetic link to common diseases by SNP mapping or direct association. Technology developments focused on rapid, high-throughput, and low cost DNA sequencing would facilitate the understanding and use of genetic information, such as SNPs, in applied medicine.

In general, 10%-to-15% of SNPs will affect protein function by altering specific amino acid residues, will affect the proper processing of genes by changing splicing mechanisms, or will affect the normal level of expression of the gene or protein by varying regulatory mechanisms. It is envisioned that the identification of informative SNPs will lead to more accurate diagnosis of inherited disease, better prognosis of risk susceptibilities, or identity of sporadic mutations in tissue. One application of an individual's SNP profile would be to significantly delay the onset or progression of disease with prophylactic drug therapies. Moreover, an SNP profile of drug metabolizing genes could be used to prescribe a specific drug regimen to provide safer and more efficacious results. To accomplish these ambitious goals, genome sequencing will move into the resequencing phase with the potential of partial sequencing of a large majority of the population, which would involve sequencing specific regions or single base pairs in parallel, which are distributed throughout the human genome to obtain the SNP profile for a given complex disease.

Sequence variations underlying most common diseases are likely to involve multiple SNPs, which are dispersed throughout associated genes and exist in low frequency. Thus, DNA sequencing technologies that employ strategies for de novo sequencing are more likely to detect and/or discover these rare, widely dispersed variants than technologies targeting only known SNPs.

Traditionally, DNA sequencing has been accomplished by the "Sanger" or "dideoxy" method, which involves the chain termination of DNA synthesis by the incorporation of 2',3'-dideoxynucleotides (ddNTPs) using DNA polymerase (Sanger, F., Nicklen, S., and Coulson, A. R. (1977) DNA sequencing with chain-terminating inhibitors. Proc. Natl. Acad. Sci. USA 74, 5463-5467). The reaction also includes the natural 2'-deoxynucleotides (dNTPs), which extend the DNA chain by DNA synthesis. Balanced appropriately, competition between chain extension and chain termination results in the generation of a set of nested DNA fragments, which are uniformly distributed over thousands of bases and differ in size as base pair increments. Electrophoresis is used to resolve the nested DNA fragments by their respective size. The ratio of dNTP/ddNTP in the sequencing reaction determines the frequency of chain termination, and hence the distribution of lengths of terminated chains. The fragments are then detected via the prior attachment of four different fluorophores to the four bases of DNA (i.e., A, C, G, and T), which fluoresce their respective colors when irradiated with a suitable laser source. Currently, Sanger sequencing has been the most widely used method for discovery of SNPs by direct PCR sequencing (Gibbs, R. A., Nguyen, P.-N., McBride, L. J., Koepf, S. M., and Caskey, C. T. (1989) Identification of mutations leading to the Lesch-Nyhan syndrome by automated direct DNA sequencing of in vitro amplified cDNA. Proc. Natl. Acad. Sci. USA 86, 1919-1923) or genomic sequencing (Hunkapiller, T., Kaiser, R. J., Koop, B. F., and Hood, L. (1991) Large-scale and automated DNA sequencing Determination. Science 254, 59-67; International Human Genome Sequencing Consortium. Initial sequencing and analysis of the human genome. (2001) Nature 409, 860-921).

The need for developing new sequencing technologies has never been greater than today with applications spanning diverse research sectors including comparative genomics and evolution, forensics, epidemiology, and applied medicine for diagnostics and therapeutics. Current sequencing technologies are too expensive, labor intensive, and time consuming for broad application in human sequence variation studies. Genome center cost is calculated on the basis of dollars per 1,000 $Q_{20}$ bases and can be generally divided into the categories of instrumentation, personnel, reagents and materials, and overhead expenses. Currently, these centers are operating at less than one dollar per 1,000 $Q_{20}$ bases with at least 50% of the cost resulting from DNA sequencing instrumentation alone. Developments in novel detection methods, miniaturization in instrumentation, microfluidic separation technologies, and an increase in the number of assays per run will most likely have the biggest impact on reducing cost.

It is therefore an object of the invention to provide novel compounds that are useful in efficient sequencing of genomic information in high throughput sequencing reactions.

It is another object of the invention to provide novel reagents and combinations of reagents that can efficiently and affordably provide genomic information.

It is yet another object of the invention to provide libraries and arrays of reagents for diagnostic methods and for developing targeted therapeutics for individuals.

SUMMARY

Provided are nucleoside compounds as well as phosphates and salts thereof, that can be used in DNA sequencing technology. The compounds are optionally in the form of ribonucleoside triphosphate (NTP) and deoxyribonucleoside triphosphate (dNTP) compounds. The nucleotide and nucleoside compounds include a noncleavable group labeled with a fluorescent dye. The nucleotide and nucleoside compounds are designed to terminate DNA synthesis, so that nucleic acid oligomers can be sequenced rapidly in a parallel format.

A variety of nucleotide and nucleoside compounds, containing the nucleobases adenine, cytosine, guanine, thymine, uracil, or naturally occurring derivatives thereof, are provided that can be derivatized to include a detectable label such as a dye.

In one embodiment the base of the nucleoside is covalently attached with a benzyl group, and the alpha carbon position of the benzyl group is optionally substituted with one alkyl or aryl group as described herein. The benzyl group can be functionalized to enhance the termination properties. The termination properties of the optionally alpha carbon substituted benzyl group attached to the nucleobase occur even when the 3'-OH group on the ribose sugar is unblocked. These 3'-OH unblocked terminators are well-tolerated by a number of commercially available DNA polymerases, representing a key advantage over 3'-O-blocked terminators. The linker group also can be derivatized to include a selected fluorescent dye.

In particular, methods for DNA sequencing are provided using combinations of the four nucleoside triphosphate compounds, modified with a non-cleavable terminating group, and derivatives described herein and labeled with distinct fluorescent dyes, which could be used for identifying the incorporated bases to reveal the underlying DNA sequence.

DETAILED DESCRIPTION

Provided are nucleotide and nucleoside compounds as well as salts, esters and phosphates thereof, that can be used in rapid DNA sequencing technology. The compounds are optionally in the form of ribonucleoside triphosphates (NTPs) and deoxyribonucleoside triphosphates (dNTP). The nucleotide and nucleoside compounds in one embodiment includes a non-cleavable group labeled with a fluorescent dye. The nucleotide and nucleoside compounds are designed to terminate DNA synthesis, so that these monomers can be used for rapid sequencing in a parallel format. The presence of such groups labeled with fluorescent dyes on the nucleotide and nucleoside compounds can enhance the speed and accuracy of sequencing of large oligomers of DNA in parallel, to allow, for example, rapid whole genome sequencing, and the identification of polymorphisms and other valuable genetic information.

A variety of nucleotide and nucleoside compounds, containing the nucleobases adenine, cytosine, guanine, thymine, uracil, or naturally occurring derivatives thereof, are provided that include non-cleavable terminating moieties and/or which can be derivatized to include a detectable label such as a dye.

In one embodiment, the nucleobases adenine, cytosine, guanine, thymine, uracil, or naturally occurring derivatives thereof, can be covalently attached to a dye via a non-cleavable terminating moiety. The non-cleavable terminating moiety can be derivatized to enhance its termination of DNA synthesis thus increasing its usefulness in DNA sequencing.

I. Advantages of Compounds for Sequencing

Nucleotide and nucleoside compounds are provided which are useful in DNA sequencing technology. The efficiency of incorporation of compounds according to the invention may range from about 70% to about 100% of the incorporation of the analogous native nucleoside. Preferably, the efficiency of incorporation will range from about 85% to about 100%. Further, termination of nucleic acid extension will range from about 90% to about 100% upon incorporation of compounds according to the invention. Nucleotide and nucleoside compounds in one embodiment have a termination efficiency of at least 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9%.

II. Compounds

A variety of nucleosides and compounds as well as their mono, di and triphosphates are provided. The compounds are useful for sequencing technology. In one embodiment, the nucleoside compound includes a fluorescent group that can be detected efficiently. The nucleoside compounds can be converted into their respective triphosphates for DNA polymerase reactions. Compounds according to the invention may be represented by the following formula:

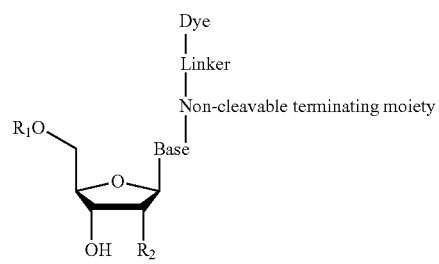

wherein $R_1$ is H, monophosphate, diphosphate or triphosphate, $R_2$ is H or OH, base is cytosine, uracil, thymine, adenine, guanine, or a naturally occurring derivative thereof, the non-cleavable terminating moiety is a group imparting polymerase termination properties to the compound, linker is a bifunctional group, and the dye is a fluorophore. Compounds according to the invention can be designed as fluorescent, non-labile nonreversible terminators useful in DNA synthesis sequencing.

In one embodiment, a compound is provided having a structure of formulas I-VII:

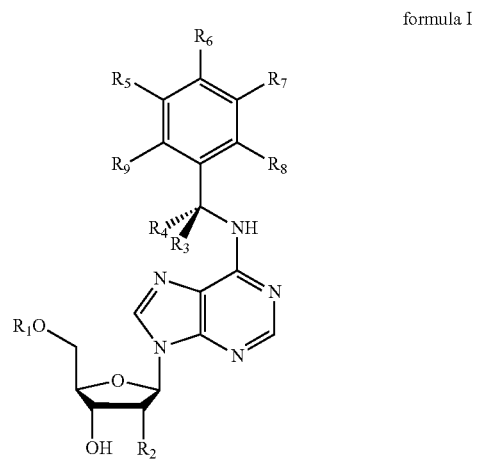

formula I

-continued formula II
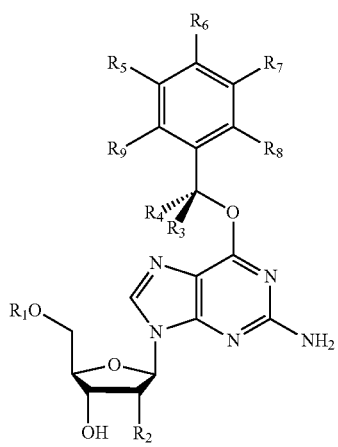

formula III
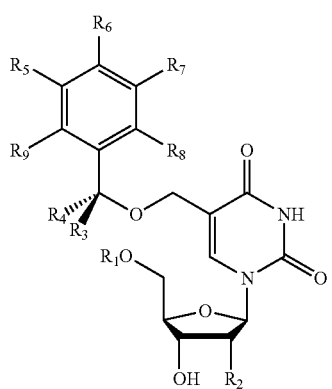

formula IV
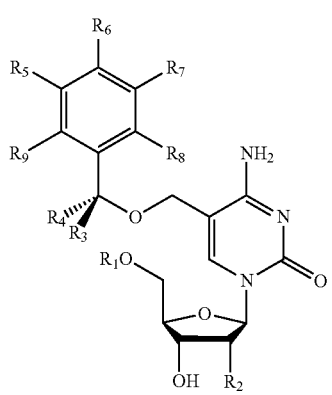

-continued formula V
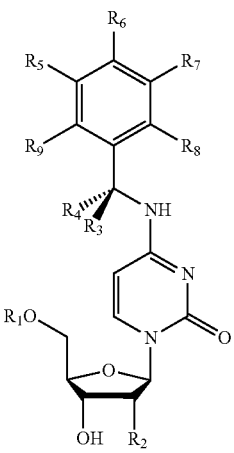

formula VI
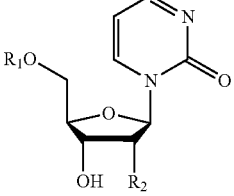

formula VII
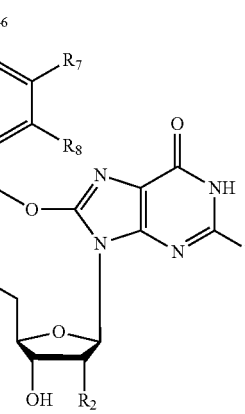

wherein $R_1$=H, monophosphate, diphosphate or triphosphate, $R_2$=H or OH, $R_3$ and $R_4$ are each independently selected from the group of H, a $C_1$-$C_{12}$ straight chain or branched alkyl, a $C_2$-$C_{12}$ straight chain or branched alkenyl or polyenyl, a $C_2$-$C_{12}$ straight chain or branched alkynyl or polyalkynyl, and an aromatic group such as a phenyl, naphthyl, or pyridine ring, $R_5$, $R_6$, and $R_7$, are each independently selected from the group H, $OCH_3$, $NO_2$, CN, a halide, a $C_1$-$C_{12}$ straight chain or branched alkyl, a $C_2$-$C_{12}$ straight chain or branched alkenyl or polyenyl, a $C_2$-$C_{12}$ straight chain or branched alkynyl or polyalkynyl, an aromatic group such as a phenyl, naphthyl, or pyridine ring, and/or a linker group of the general structure:

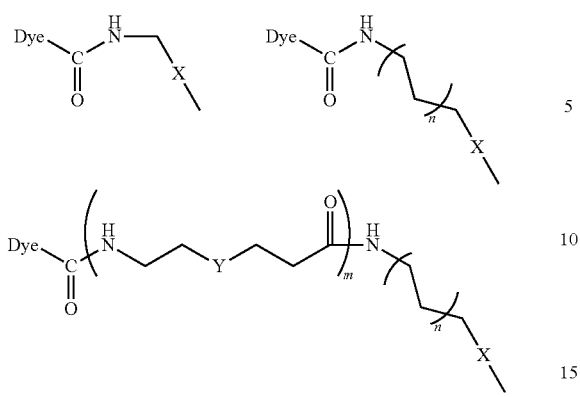

X=CH$_2$, CH=CH, C≡C, O, S, or NH, Y=CH$_2$, O, or NH, n=an integer from 0-12; m=an integer from 0-12, and Dye=a fluorophore, and R$_8$ and R$_9$ are as defined above for R$_5$, R$_6$, and R$_7$, with the proviso that R$_8$ and R$_9$ are not NO$_2$, or pharmaceutically acceptable salt or ester thereof or enantiomer, racemic mixture, or stereoisomer thereof.

In a preferred embodiment, R$_3$ and R$_4$ are selected from the group consisting of, but not limited to, —CH$_3$, —CH$_2$CH$_3$, —CH$_2$CH$_2$CH$_3$, isopropyl, tert-butyl, and phenyl. Alternatively, R$_3$ and R$_4$ are selected from the group consisting of, but not limited to, alkyl and aromatic groups optionally containing at least one heteroatom in the alkyl or aromatic groups, and further wherein the aromatic group may optionally be an aryl such as phenyl or polycyclic such as a naphthyl group. In certain embodiments, R$_5$, R$_6$, R$_7$, and R$_8$ are selected from an aromatic group consisting of aryl and polycyclic groups.

Alternatively, non-cleavable terminating moieties may have the following general structures:

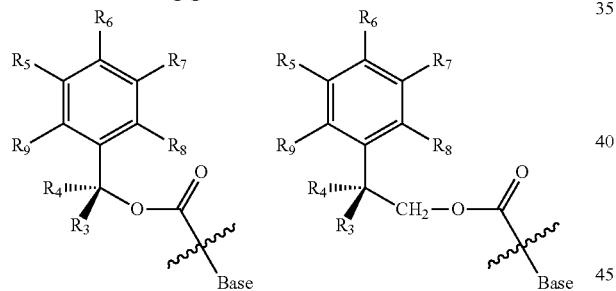

For example, compounds with such linkers non-cleavable terminating moieties could have the following structures:

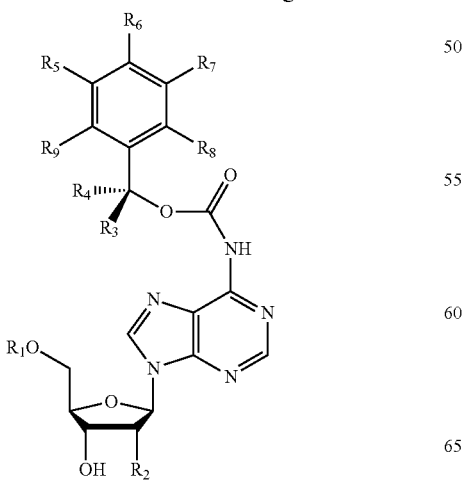

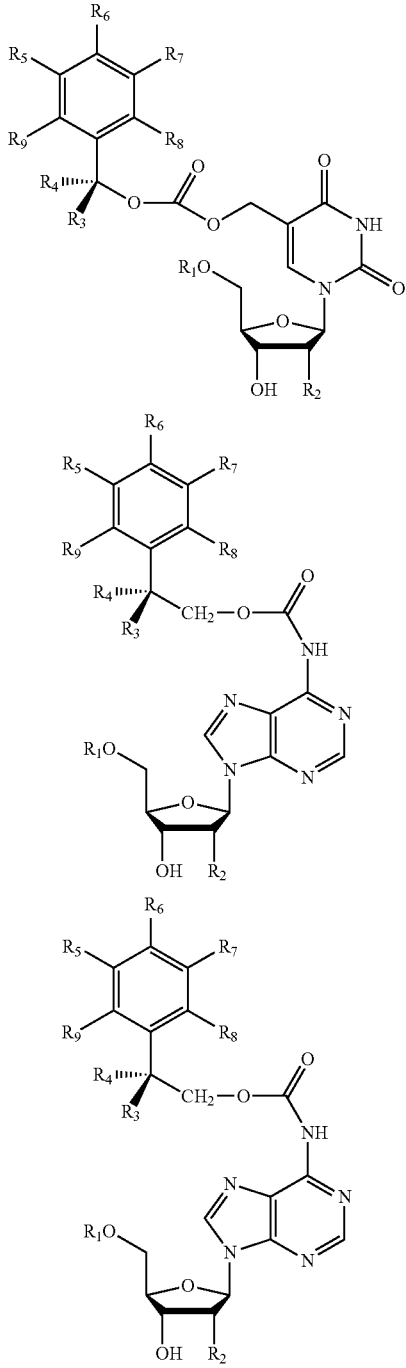

wherein the noncleavable terminating moiety can be attached to the base through a linkage such as a benzyl amine, benzyl ether, carbamate, carbonate, 2-(o-nitrophenyl)ethyl carbamate, and/or 2-(o-nitrophenyl)ethyl carbonate.

Fluorescent dyes are not particularly limited. For example, the fluorophore may be selected from the group consisting of, but not limited to, BODIPY, fluorescein, rhodamine, coumarin, xanthene, cyanine, pyrene, phthalocyanine, phycobiliprotein, alexa, squarene dye, combinations resulting in energy transfer dyes, and derivatives thereof.

Preferred embodiments include but are not limited to the following compounds:

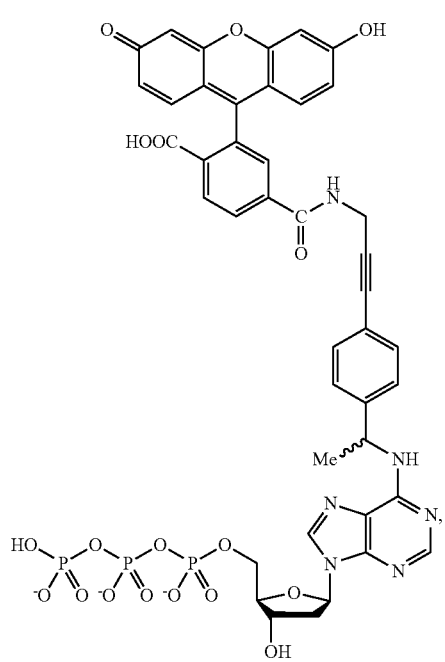
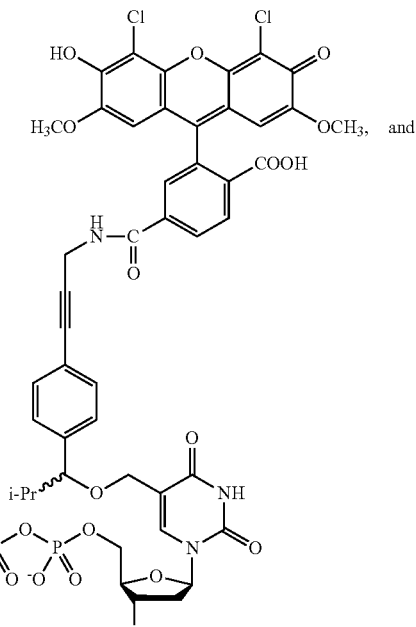
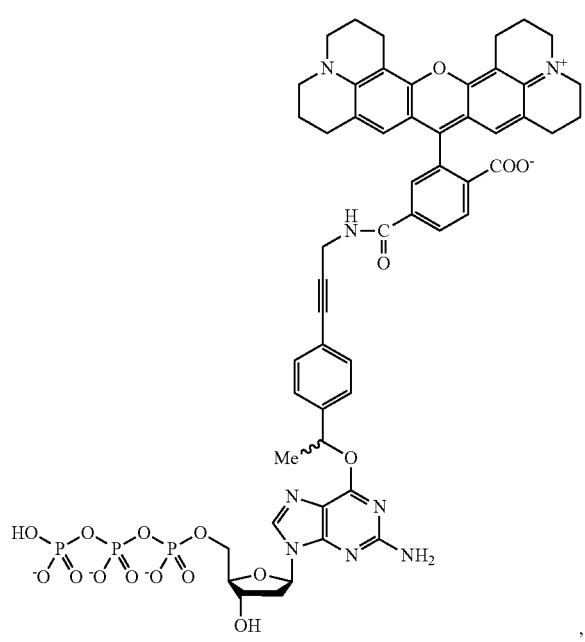
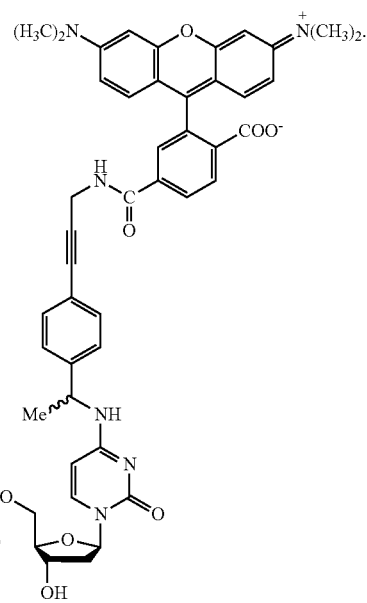
III. Synthesis of Compounds
The compounds disclosed herein can be synthesized generally as disclosed herein, and using methods available in the art. For example, the following general scheme represents the synthesis of an adenosine compound:

General Scheme for synthesis of an Adenosine N6-modified compound

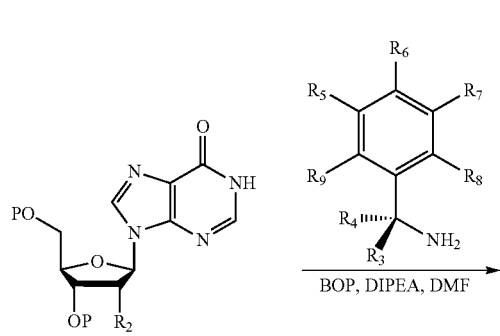

P denotes a suitable
protecting group
R$_2$ = H or OH group
with a suitable
protecting group

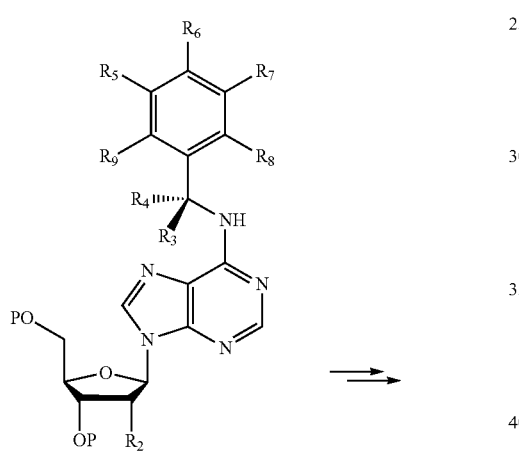

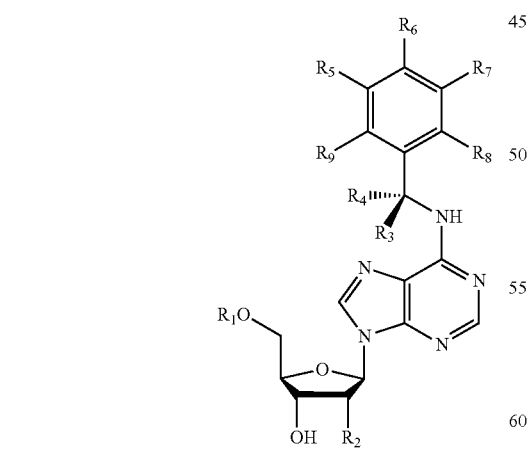

R$_1$ to R$_8$ has the same
definition as
defined for the
general structure

General Scheme for synthesis Guanosine O6-modified compounds

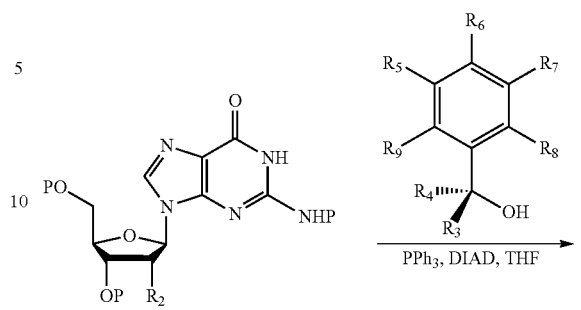

P denotes a suitable protecting group
R$_2$ = H or OH group with a suitable
protecting group

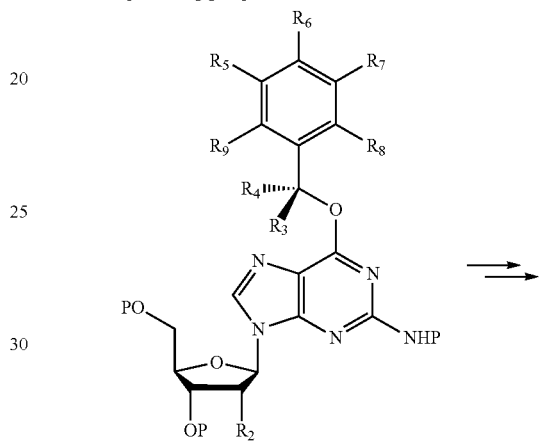

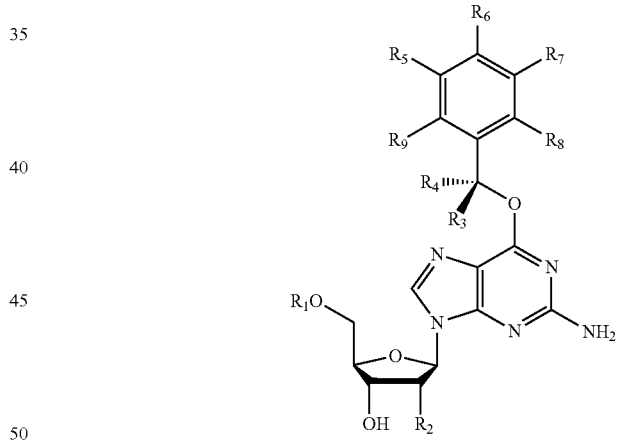

R$_1$ to R$_8$ has the same definition as
defined for the general structure

General Scheme for synthesis Guanosine 8-Oxo-modified compounds

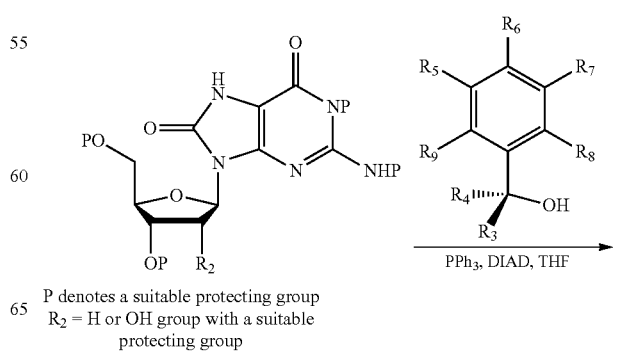

P denotes a suitable protecting group
R$_2$ = H or OH group with a suitable
protecting group

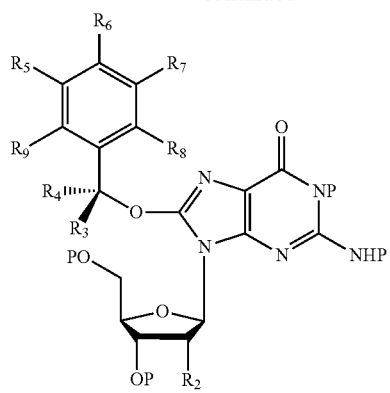

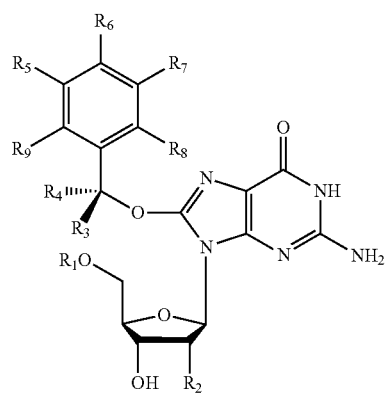

R₁ to R₈ has the same definition as defined for the general structure

General Scheme for synthesis Uridine 5-HOMe-modified compounds

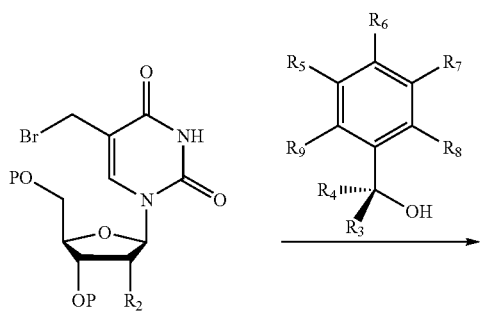

P denotes a suitable protecting group
R₂ = H or OH group with a suitable protecting group

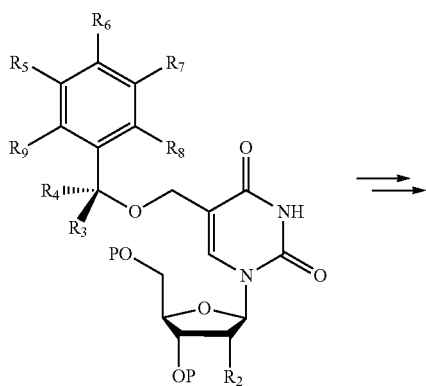

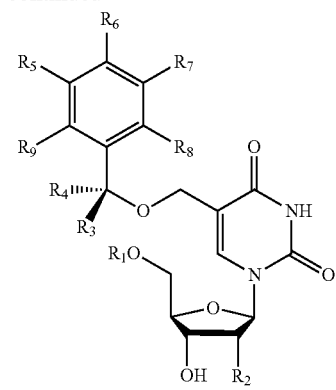

R₁ to R₈ has the same definition as defined for the general structure

General Scheme for synthesis Cytidine 5-HOMe-modified compounds

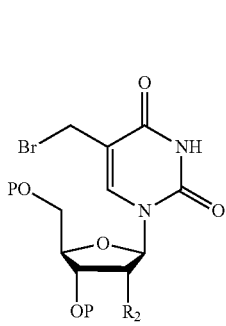 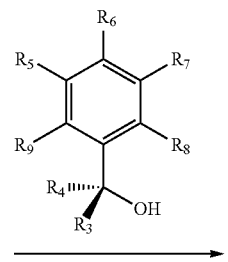

P denotes a suitable protecting group
R₂ = H or OH group with a suitable protecting group

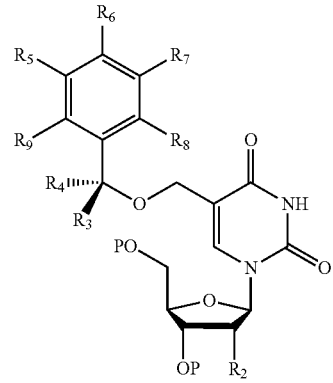

i. TPSCl, DMAP, Et₃N, CH₂Cl₂
ii. NH₃, 1,4-dioxane

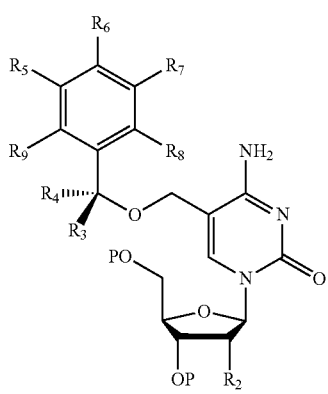

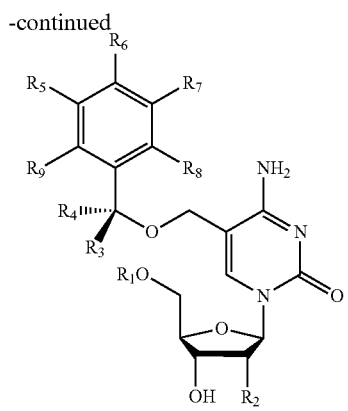

$R_1$ to $R_8$ has the same definition as defined for the general structure

General Scheme for synthesis Cytidine N4-modified compounds

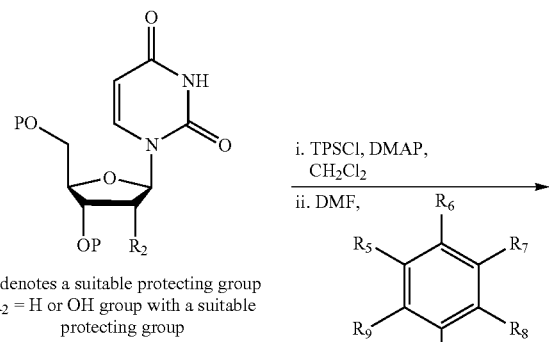

P denotes a suitable protecting group
$R_2$ = H or OH group with a suitable protecting group

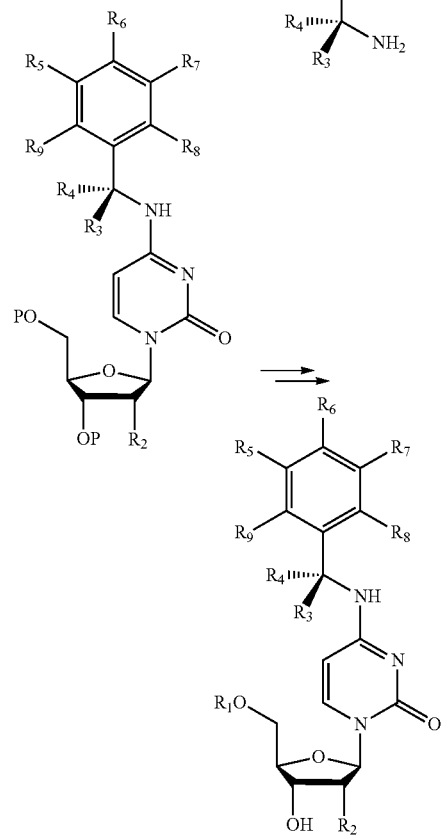

$R_1$ to $R_8$ has the same definition as defined for the general structure

Additional details are provided in the Examples section.

IV. Methods of Use of Compounds According to the Invention

The nucleoside compounds disclosed herein can be used in for a variety of purposes in DNA sequencing technology. Polymerases used in conjunction with the compounds according to the invention may be native polymerases or modified polymerases. Polymerases include DNA and non-DNA polymerases. For example, polymerases for use with the compounds according to the invention include without limitation reverse transcriptase, terminal transferase, and DNA polymerase. Among DNA polymerases, preferred embodiments include Taq DNA polymerase, Klenow(-exo-) DNA polymerase, Bst DNA polymerase, VENT® (exo-) DNA polymerase (DNA polymerase A cloned from *Thermococcus litoralis* and containing the D141A and E143A mutations), Pfu(-exo-) DNA polymerase, and DEEPVENT™ (exo-) DNA polymerase (DNA polymerase A, cloned from the *Pyrococcus* species GB-D, and containing the D141A and E143A mutations). Modified polymerases include without limitation AMPLITAQ® DNA polymerase, FS (Taq DNA polymerase that contains the G46D and F667Y mutations), THERMOSEQUENASE™ DNA polymerase (Taq DNA polymerase that contains the F667Y mutation), THERMOSEQUENASE™ II DNA polymerase (blend of THERMOSEQUENASE™ DNA polymerase and *T. acidophilum* pyrophosphatase), THERMINATOR™ DNA polymerase (DNA polymerase A, cloned from the *Thermococcus* species 9° N-7 and containing the D141A, E143A and A485L mutations), THERMINATOR™ II DNA polymerase (THERMINATOR™ DNA polymerase that contains the additional Y409V mutation), and VENT® (exo-) A488L DNA polymerase (VENT® (exo-) DNA polymerase that contains the A488L mutation). Preferably, compounds according to the invention are incorporated at levels equal to or near the incorporation levels of naturally-occurring nucleotides, thus resulting in no bias against the compounds according to the invention. Even more preferably, compounds according to the invention are compatible with commercially-available polymerases.

In a preferred embodiment, methods according to the invention include a method of determining the sequence of a target nucleic acid comprising (i) adding a target nucleic acid to a Sanger or Sanger-type sequencing apparatus, (ii) adding one or more compounds according to the invention to the sequencing apparatus, with the proviso that where more than one type of base is present, each base is attached to a different fluorophore; (iii) adding a complementary primer and a polymerase enzyme, (iv) performing a polymerase reaction to incorporate at least one of the compounds of step (ii) into a growing nucleic acid strand, and (v) analyzing the result of the Sanger sequencing reaction with fluorescence sequencing instrumentation or by pulsed multiline excitation fluorescence, wherein steps (i)-(iii) can be performed in any order.

In a preferred embodiment, incorporation of at least one compound according to step (iv) is followed by termination of strand growth at an efficiency of from about 90% to about 100%. Alternatively, the incorporation of at least one compound according to step (iv) occurs at about 70% to about 100% of the efficiency of incorporation of a native substrate with the same base in the polymerase reaction, or more preferably at about 85% to about 100%.

Methods according to the invention also include a method of incorporating a non-naturally occurring component into a nucleic acid comprising: (i) adding a target nucleic acid to a sequencing apparatus; (ii) adding one or more compounds according to the invention to the sequencing apparatus, with the proviso that where more than one type of base is present, each base is attached to a different fluorophore; (iii) adding a polymerase enzyme; and (iv) performing a polymerase reaction to incorporate at least one of the compounds of step (ii) into a growing nucleic acid strand, wherein steps (i)-(iii) can be performed in any order. The method can further comprise (v) analyzing the result of the polymerase chain reaction for incorporation of at least one compound from step (ii).

An alternative embodiment of the invention is a method of terminating nucleic acid synthesis comprising the step of placing a 3'-OH unprotected nucleotide or nucleoside according to the invention in the environment of a polymerase and allowing incorporation of the 3'-OH unprotected nucleotide or nucleoside into a nucleic acid. Preferred embodiments of the method have an efficiency of termination upon incorporation of the 3'-OH unprotected nucleotide or nucleoside ranging from about 90% to about 100%; with the efficiency of incorporation of the 3'-OH unprotected nucleotide or nucleoside ranging from about 70% to about 100% compared to the efficiency of incorporation of a naturally-occurring nucleotide or nucleoside with the same base.

Methods of performing Sanger or Sanger-type sequencing comprising addition of a compound according to the invention to a Sanger or Sanger-type sequencing method are also encompassed. A method of performing mini-sequencing or minisequencing-type sequencing comprising addition of a compound according to the invention to a mini-sequencing or minisequencing-type sequencing method is within the scope of the invention.

PME Detector

In one embodiment, a pulsed-multiline excitation ("PME") for color-blind fluorescence detection can be used as described in US 2003/0058440 published Mar. 27, 2003, or PCT WO 03/021212. published Mar. 13, 2003. This technology provides fluorescence detection with application for high-throughput identification of informative SNPs, for more accurate diagnosis of inherited disease, better prognosis of risk susceptibilities, or identification of sporadic mutations. The PME technology has two main advantages that significantly increase fluorescence sensitivity: (1) optimal excitation of all fluorophores in the genomic assay and (2) "color-blind" detection, which collects considerably more light than standard wavelength resolved detection. This technology differs significantly from DNA sequencing instrumentation which features single source excitation and color dispersion for DNA sequence identification. The technology can be used in clinical diagnostics, forensics, and general sequencing methodologies and will have the capability, flexibility, and portability of targeted sequence variation assays for a large majority of the population.

In one embodiment, an apparatus and method for use in high-throughput DNA sequence identification is used. A pulse-multiline excitation apparatus for analyzing a sample containing one or more fluorescent species is used, comprising: one or more lasers configured to emit two or more excitation lines, each excitation line having a different wavelength; a timing circuit coupled to the one or more lasers and configured to generate the two or more excitation lines sequentially according to a timing program to produce time-correlated fluorescence emission signals from the sample; a non-dispersive detector positioned to collect the time-correlated fluorescence emission signals emanating from the sample; and an analyzer coupled to the detector and configured to associate the time-correlated fluorescence emission signals with the timing program to identify constituents of the sample.

The detector and the analyzer may be integral. In one embodiment, the two or more excitation lines intersect at the sample, or the two or more excitation lines may be configured so that they do not intersect in the sample. The two or more excitation lines may be coaxial.

In one embodiment, the apparatus may further comprise an assembly of one or more prisms in operative relation with the one or more lasers and configured to render radiation of the two or more excitation lines substantially colinear and/or coaxial.

The apparatus may have a plurality of excitation lines, for example 1, 2, 3, 4, 5, 6, 7, 8, 9, 10, 11, 12, 13, 14, 15, 16 or more excitation lines having 1, 2, 3, 4, 5, 6, 7, 8, 9, 10, 11, 12, 13, 14, 15, 16 or more excitation wavelengths, respectively. The sample may be comprised a plurality of vessels such as capillaries, for example in 1, 2, 3, 4, 5, 6, 7, 8, 9, 10, 11, 12, 13, 14, 15, 16, up to 20, up to 24, up to 28, up to 36, up to 48, up to 64, up to 96, up to 384 or more capillaries. A sheath flow cuvette may be used.

The timing program may comprise a delay between the firing of each laser of between about 10 fs and about 5 s, between about 1 ms and about 100 ms, or between about 50 ps and about 500 ps. One or more of the excitation lines is pulsed. The pulsed excitation line may be controlled by TTL logic or by mechanical or electronic means. In one embodiment, the apparatus may generate a sequence of discrete excitation lines that are time-correlated with the fluorescence emission signals from the sample.

The lasers may independently comprise a diode laser, a semiconductor laser, a gas laser, such as an argon ion, krypton, or helium-neon laser, a diode laser, a solid-state laser such as a Neodymium laser which will include an ion-gain medium, such as YAG and yttrium vanadate ($YVO_4$), or a diode pumped solid state laser. Other devices, which produce light at one or more discrete excitation wavelengths, may also be used in place of the laser. The laser may further comprise a Raman shifter in operable relation with at least one laser beam. In one embodiment of the invention, the excitation wavelength provided by each laser is optically matched to the absorption wavelength of each fluorophore.

The detector may comprise a charged couple device, a photomultiplier tube, a silicon avalanche photodiode or a silicon PIN detector. The footprint of the device is preferably small, such as less than 4 ft×4 ft×2 ft, less than 1 ft×1 ft×2 ft, and could be made as small as 1 in×3 in×6 in.

Another aspect comprises a method of identifying sample components comprising: (a) preparing a sample comprising sample components, a first dye and a second dye; (b) placing the sample in the beam path of a first excitation line and a second excitation line; (c) sequentially firing the first excitation line and the second excitation line; (d) collecting fluorescence signals from the samples as a function of time; and (e) sorting the fluorescence by each excitation line's on-time window, wherein the sample components are identified. It is an aspect of the invention that the fluorescence signals are collected from discrete time periods in which no excitation line is incident on the sample, the time periods occurring between the firing of the two excitation lines. This technique is known as "looking in the dark." Yet another aspect is that the absorption maximum of the first dye substantially corresponds to the excitation wavelength of the first excitation line. The absorption maximum of the second dye may also substantially corresponds to the excitation wavelength of the second excitation line. In yet another aspect there is a third and fourth dye and a third and fourth excitation line, wherein the absorption maxima of the third and fourth dyes substantially correspond to the excitation wavelengths of the third and four excitation lines, respectively. Similarly, there may be 5, 6, 7, 8, 9, 10, 11, 12, 13, 14, 15, 16 or more dyes wherein the absorption maxima of the dyes substantially corresponds to excitation wavelengths of a 5th, 6th, 7th, 8th, 9th, 10th, 11th, 12th, 13th, 14th, or more excitation lines, respectively. The dyes may be a zanthene, fluorescein, rhodamine, BODIPY, cyanine, coumarin, pyrene, phthalocyanine, phycobiliprotein, ALEXA FLUOR® (e.g., (ALEXA FLUOR® 350, ALEXA FLUOR® 405, ALEXA FLUOR® 430, ALEXA FLUOR® 488, ALEXA FLUOR® 514, ALEXA FLUOR® 532, ALEXA FLUOR® 546, ALEXA FLUOR® 555, ALEXA FLUOR® 568, ALEXA FLUOR® 568, ALEXA FLUOR® 594, ALEXA FLUOR® 610, ALEXA FLUOR® 633, ALEXA FLUOR® 647, ALEXA FLUOR® 660, ALEXA FLUOR® 680, ALEXA FLUOR® 700 or ALEXA FLUOR® 750)), squariane dyes, or some other suitable dye.

In one embodiment, sample components enable the determination of SNPs. The method may be for the high-throughput identification of informative SNPs. The SNPs may be obtained directly from genomic DNA material, from PCR amplified material, or from cloned DNA material and may be assayed using a single nucleotide primer extension method. The single nucleotide primer extension method may comprise using single unlabeled dNTPs, single labeled dNTPs, single 3'-modified dNTPs, single base-modified 2'-dNTPs, single alpha-thio-dNTPs or single labeled 2',3' dideoxynucleotides. The mini-sequencing method may comprise using single unlabeled dNTPs, single labeled dNTPs, single 3'-modified dNTPs, single base-modified 2'-dNTPs, single alpha-thio-dNTPs or single labeled 2',3'-dideoxynucleotides. The SNPs may be obtained directly from genomic DNA material, from PCR amplified material, or from cloned DNA materials.

Also envisioned are methods for detecting nucleic acids. Nucleic acids may be detected in situ or in various gels, blots, and similar methods for detecting nucleic acids, such as disclosed in U.S. Pat. No. 7,125,660, which is incorporated herein by reference.

EXAMPLES

Example 1 dA Compounds

Synthesis of $N^6$-benzyl-2'-deoxyadenosine triphosphate (WW2p062)

Scheme. Synthesis or $N^6$-benzyl-2'-deoxyadenosine-5'-triphosphate.

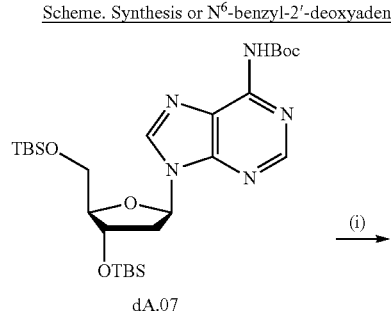

dA.07

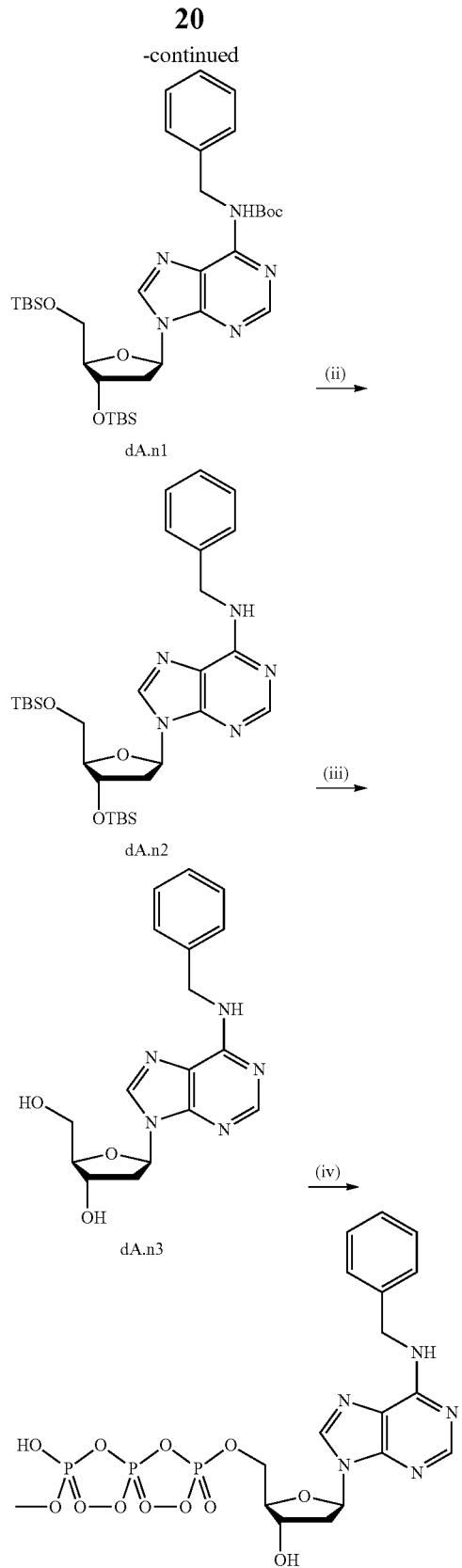

(i) NaH, DMF, benzyl bromide, 0° C., then gradually warmed to room temperature, 86%; (ii) SiO$_2$, vacuum, 70-80° C., 95%; (iii) n-Bu$_4$NF, THF, 99%; (iv) POCl$_3$, (MeO)$_3$PO, minus 20-30° C.; (n-Bu$_3$NH)$_2$H$_2$P$_2$O$_7$, n-Bu$_3$N, DMF; 1 M HNEt$_3$HCO$_3$; 32%.

$N^6$-tert-Butyloxycarbonyl-$N^6$-benzyl-3',5'-O-bis-tert-butyldimethylsilyl-2'-deoxyadenosine (dA.n1)

NaH (18 mg, 0.75 mmol, dry) was added to a solution of compound dA.07 (400 mg, 0.58 mmol) in anhydrous DMF (5 mL) at 0° C. and stirred for 30 minutes. A solution of benzyl bromide (149 mg, 0.87 mmol) in anhydrous DMF (2.5 mL) was added dropwise. The mixture was gradually warmed to room temperature and stirred for two hours. DMF was removed in vacuo, and the residue was dissolved in ethyl acetate (60 mL), washed twice with saturated $NH_4Cl$ solution (40 mL each) and once with water (40 mL). The combined aqueous layer was extracted with ethyl acetate (10 mL), and the combined organic layer was dried over $Na_2SO_4$, concentrated in vacuo, and purified by silica gel column chromatography to yield $N^6$-tert-butyloxycarbonyl-$N^6$-benzyl-3',5'-O-bis-tert-butyldimethylsilyl-2'-deoxyadenosine dA.n1 (398 mg, 86%) as a viscous oil.

$^1$H NMR (400 MHz, $CDCl_3$): δ 8.72 (s, 1H, H-8), 8.32 (s, 1H, H-2), 7.39 (m, 2H, Ph-H), 7.25 (m, 2H, Ph-H), 7.18 (m, 1H, Ph-H), 6.49 (t, 1H, J=6.4 Hz, H-1'), 5.28 (s, 2H, Ph-$CH_2$), 4.62 (m, 1H, H-3'), 4.01 (m, 1H, H-4'), 3.85 (dd, 1H, J=4.4 and 11.2 Hz, H-5'a), 3.77 (dd, 1H, J=3.4 and 11.2 Hz, H-5'b), 2.61 (m, 1H, H-2'a), 2.43 (m, 1H, H-2'b), 1.65 (s, 9H, $(CH_3)_3$CO), 0.96 (s, 18H, $(CH_3)_3$CSi), 0.08 (2 s, 12H, $(CH_3)_2$Si).

$N^6$-Benzyl-3',5'-O-bis-tert-butyldimethylsilyl-2'-deoxyadenosine (dA.n2)

Silica gel 60 (3.76 g, 100-200 mesh, activated by heating to 70-80° C. under reduced pressure for hours) was added to a solution of compound dA.n1 (376 mg, 0.56 mmol) in $CH_2Cl_2$ (20 mL), and the mixture was evaporated in vacuo to dryness. The residue was heated to 70-80° C. under reduced pressure for two days, washed three times with methanol (30 mL each), and filtered using a buchi funnel. The combined filtrate was concentrated in vacuo and purified by silica gel column chromatography to yield $N^6$-benzyl-3',5'-O-bis-tert-butyldimethylsilyl-2'-deoxyadenosine dA.n2 (305 mg, 95%) as a yellow foam.

$^1$H NMR (400 MHz, $CDCl_3$): δ 8.41 (s, 1H, H-8), 8.07 (s, 1H, H-2), 7.38 (m, 2H, Ph-H), 7.33 (m, 2H, Ph-H), 7.28 (m, 1H, Ph-H), 6.45 (t, 1H, J=6.4 Hz, H-1'), 6.12 (br s, 1H, 6-NH), 4.87 (br s, 2H, Ph-$CH_2$), 4.62 (m, 1H, H-3'), 4.01 (m, 1H, H-4'), 3.87 (dd, 1H, J=4.2 and 11.2 Hz, H-5'a), 3.77 (dd, 1H, J=3.2 and 11.2 Hz, H-5'b), 2.64 (m, 1H, H-2'a), 2.44 (m, 1H, H-2'b), 0.91 (s, 18H, $(CH_3)_3$CSi), 0.09 (2 s, 12H, $(CH_3)_2$Si—).

$N^6$-Benzyl-2'-deoxyadenosine (dA.n3)

A solution of n-$Bu_4NF$ (335 mg, 1.28 mmol) in THF (2.5 mL) was added to a solution of compound dA.n2 (292 mg, 0.51 mmol) in THF (6 mL) at 0° C. The reaction mixture was gradually warmed to room temperature and stirred for two hours. Silica gel 60 (1 g) was added, and the mixture was evaporated in vacuo to dryness. The residue was purified by silica gel column chromatography to yield $N^6$-benzyl-2'-deoxyadenosine dA.n3 (173 mg, 99%) as a white foam.

$^1$H NMR (400 MHz, $CD_3OD$): δ 8.30 (s, 1H, H-8), 8.25 (s, 1H, H-2), 7.36 (m, 2H, Ph-H), 7.31 (m, 2H, Ph-H), 7.24 (m, 1H, Ph-H), 6.42 (dd, 1H, J=6.0 and 7.9 Hz, H-1'), 4.81 (br s, 2H, Ph-$CH_2$), 4.57 (m, 1H, H-3'), 4.06 (m, 1H, H-4'), 3.83 (m, 1H, J=2.9 and 12.3 Hz, H-5'a), 3.73 (dd, 1H, J=3.3 and 12.3 Hz, H-5'b), 2.79 (m, 1H, H-2'a), 2.40 (m, 1H, H-2'b).

$N^6$-Benzyl-2'-deoxyadenosine-5'-triphosphate (WW2p062)

$POCl_3$ (22 μL, 0.24 mmol) was added to a solution of compound dA.10a (42 mg, 0.12 mmol) in trimethylphosphate (0.5 mL) and maintained at minus 20-30° C. for two hours. A solution of bis-tri-n-butylammonium pyrophosphate (285 mg, 0.6 mmol) and tri-n-butylamine (120 μL) in anhydrous DMF (1.2 mL) was added. After five minutes of stirring, triethylammonium bicarbonate buffer (1 M, pH 7.5; 10 mL) was added. The reaction was stirred at room temperature for one hour and then lyophilized to dryness. The residue was dissolved in water (10 mL), filtered, and purified by anion exchange chromatography using a Q Sepharose FF column (2.5×20 cm) with a linear gradient of $NH_4HCO_3$ (50 mM to 500 mM in 300 minutes) at a flow rate of 4.5 mL/min. The fractions containing triphosphate were combined and lyophilized to give $N^6$-benzyl-2'-deoxyadenosine-5'-triphosphate WW2p062 (24 mg, 32%) as a white fluffy solid.

$^1$H NMR (400 MHz, $D_2O$): δ 8.43 (s, 1H, H-8), 8.20 (s, 1H, H-2), 7.39-7.30 (m, 5H, Ph-H), 6.50 (t, 1H, J=6.4 Hz, H-1'), 4.85 (s, 2H, Ph-$CH_2$), 4.31 (s, 1H, H-4'), 4.22 (m, 2H, H-5'a and H-5'b), 2.82 (m, 1H, H-2'a), 2.62 (m, 1H, H-2'b);

$^{31}$P NMR (162 MHz, $D_2O$): δ −5.72 (d, J=15.9 Hz), −10.78 (d, J=15.4 Hz), −19.16 (t, J=14.9 Hz);

ToF-MS (ESI): For the molecular ion $C_{17}H_{20}N_5O_{12}P_3Na$ [M−2H+Na]$^-$, the calculated mass was 602.0219, and the observed mass was 602.0363.

Synthesis of 6-FAM labeled $N^6$-[4-(3-amino-1-propyl)benzyl]-2'-deoxyadenosine triphosphate (WW2p085)

Scheme. Synthesis of 6-FAM labeled $N^6$-[4-(3-amino-1-propyl)benzyl]-2'-deoxyadenosine triphosphate.

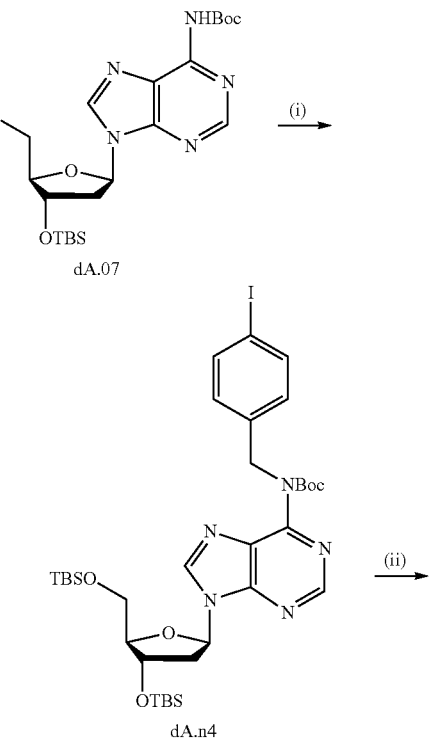

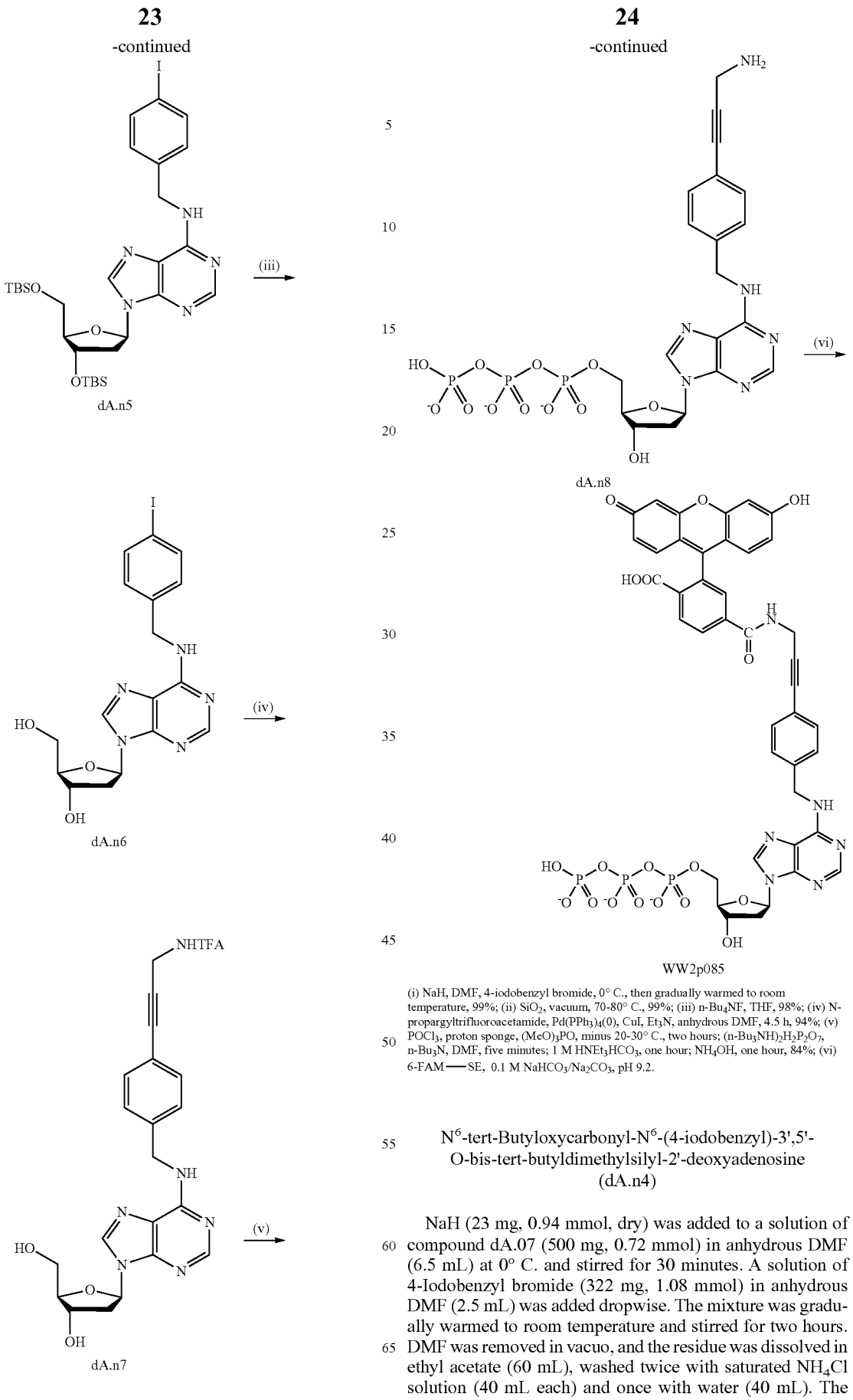

(i) NaH, DMF, 4-iodobenzyl bromide, 0° C., then gradually warmed to room temperature, 99%; (ii) SiO₂, vacuum, 70-80° C., 99%; (iii) n-Bu₄NF, THF, 98%; (iv) N-propargyltrifluoroacetamide, Pd(PPh₃)₄(0), CuI, Et₃N, anhydrous DMF, 4.5 h, 94%; (v) POCl₃, proton sponge, (MeO)₃PO, minus 20-30° C., two hours; (n-Bu₃NH)₂H₂P₂O₇, n-Bu₃N, DMF, five minutes; 1 M HNEt₃HCO₃, one hour; NH₄OH, one hour, 84%; (vi) 6-FAM—SE, 0.1 M NaHCO₃/Na₂CO₃, pH 9.2.

$N^6$-tert-Butyloxycarbonyl-$N^6$-(4-iodobenzyl)-3',5'-O-bis-tert-butyldimethylsilyl-2'-deoxyadenosine (dA.n4)

NaH (23 mg, 0.94 mmol, dry) was added to a solution of compound dA.07 (500 mg, 0.72 mmol) in anhydrous DMF (6.5 mL) at 0° C. and stirred for 30 minutes. A solution of 4-Iodobenzyl bromide (322 mg, 1.08 mmol) in anhydrous DMF (2.5 mL) was added dropwise. The mixture was gradually warmed to room temperature and stirred for two hours. DMF was removed in vacuo, and the residue was dissolved in ethyl acetate (60 mL), washed twice with saturated NH₄Cl solution (40 mL each) and once with water (40 mL). The combined aqueous layer was extracted with ethyl acetate (10 mL), and the combined organic layer was dried over $Na_2SO_4$, concentrated in vacuo, and purified by silica gel column chromatography to yield $N^6$-tert-butyloxycarbonyl-$N^6$-(4-iodobenzyl)-3',5'-O-bis-tert-butyldimethylsilyl-2'-deoxyadenosine dA.n4 (565 mg, 99%) as a viscous oil.

$^1$H NMR (400 MHz, $CDCl_3$): δ 8.71 (s, 1H, H-8), 8.33 (s, 1H, H-2), 7.58 (d, 2H, J=8.2 Hz, Ph-H), 7.17 (d, 2H, J=8.2 Hz, Ph-H), 6.49 (t, 1H, J=6.4 Hz, H-1'), 5.20 (s, 2H, Ph-$CH_2$), 4.62 (m, 1H, H-3'), 4.02 (m, 1H, H-3'), 3.86 (dd, 1H, J=4.2 and 11.2 Hz, H-5'a), 3.78 (dd, 1H, J=3.2 and 11.2 Hz, H-5'b), 2.63 (m, 1H, H-2'a), 2.45 (m, 1H, H-2'b), 1.42 (s, 9H, $(CH_3)_3$CO), 0.92 (s, 18H, $(CH_3)_3$CSi), 0.08 (2 s, 12H, $(CH_3)_2$Si—).

$N^6$-(4-Iodobenzyl)-3',5'-O-bis-tert-butyldimethylsilyl-2'-deoxyadenosine (dA.n5)

Silica gel 60 (6.00 g, 100-200 mesh, activated by heating to 70-80° C. under reduced pressure for hours) was added to a solution of compound dA.n4 (565 mg, 0.71 mmol) in $CH_2Cl_2$ (20 mL), and the mixture was evaporated in vacuo to dryness. The residue was heated to 70-80° C. under reduced pressure for two days, washed three times with methanol (30 mL each), and filtered using a buchi funnel. The combined filtrate was concentrated in vacuo and purified by silica gel column chromatography to yield $N^6$-(4-iodobenzyl)-3',5'-O-bis-tert-butyldimethylsilyl-2'-deoxyadenosine dA.n5 (489 mg, 99%) as a yellow foam.

$^1$H NMR (400 MHz, $CDCl_3$): δ 8.38 (s, 1H, H-8), 8.06 (s, 1H, H-2), 7.63 (d, 2H, J=8.2 Hz, Ph-H), 7.11 (d, 2H, J=8.2 Hz, Ph-H), 6.45 (t, 1H, J=6.4 Hz, H-1'), 6.34 (t, 1H, 6-NH), 4.81 (br s, 2H, Ph-$CH_2$), 4.61 (m, 1H, H-3'), 4.00 (m, 1H, H-4'), 3.85 (dd, 1H, J=4.2 and 11.2 Hz, H-5'a), 3.76 (dd, 1H, J=3.2 and 11.2 Hz, H-5'b), 2.64 (m, 1H, H-2'a), 2.44 (m, 1H, H-2'b), 0.91 (s, 18H, $(CH_3)_3$CSi), 0.09 (2 s, 12H, $(CH_3)_2$Si—).

$N^6$-(4-Iodobenzyl)-2'-deoxyadenosine (dA.n6)

A solution of n-$Bu_4$NF (282 mg, 1.08 mmol) in THF (1.0 mL) was added to a solution of compound dA.n5 (300 mg, 0.43 mmol) in THF (1.2 mL) at 0° C. The reaction mixture was gradually warmed to room temperature and stirred for two hours. Silica gel 60 (1 g) was added, and the mixture was evaporated in vacuo to dryness. The residue was purified by silica gel column chromatography to yield $N^6$-(4-iodobenzyl)-2'-deoxyadenosine dA.n6 (266 mg, 98%) as a white foam.

$^1$H NMR (400 MHz, DMSO-$d_6$): δ 8.48 (br s, 1H, $D_2O$ exchangeable, 6-NH), 8.40 (s, 1H, H-8), 8.27 (s, 1H, H-2), 7.68 (d, 2H, J=8.0 Hz, Ph-H), 7.17 (d, 2H, J=8.0 Hz, Ph-H), 6.39 (t, 1H, J=6.4 Hz, H-1'), 5.34 (d, 1H, $D_2O$ exchangeable, 3'-OH), 5.22 (t, 1H, $D_2O$ exchangeable, 5'-OH), 4.68 (br s, 2H, Ph-$CH_2$), 4.44 (m, 1H, H-4'), 3.91 (m, 1H, H-3'), 3.64 (m, 1H, H-5'a), 3.55 (m, 1H, H-5'b), 2.76 (m, 1H, H-2'a), 2.31 (m, 1H, H-2'b).

$N^6$-[4-(3-trifluoroacetamido-1-propynyl)benzyl]-2'-deoxyadenosine (dA.n7)

A solution of compound dA.n6 (266 mg, 0.57 mmol), N-propargyltrifluoroacetamide (260 mg, 1.72 mmol), CuI (22 mg, 0.11 mmol), tetrakis(triphenylphosphine)-palladium (0) (65 mg, 0.06 mmol), and $Et_3N$ (160 µL, 1.14 mmol) in anhydrous DMF (2.1 mL) was stirred at room temperature for 4.5 hours. The mixture was concentrated in vacuo and purified by silica gel column chromatography to yield $N^6$-[4-(3-trifluoroacetamido-1-propynyl)-benzyl]-2'-deoxyadenosine dA.n7 (268 mg, 94%) as a waxy solid.

$^1$H NMR (400 MHz, DMSO-$d_6$): δ 10.05 (br m, 1H, $D_2O$ exchangeable, NH), 8.46 (br m, 1H, $D_2O$ exchangeable, NH), 8.37 (s, 1H, H-8), 8.19 (s, 1H, H-2), 7.37 (d, 2H, J=8.2 Hz, Ph-H), 7.32 (d, 2H, J=8.2 Hz, Ph-H), 6.35 (dd, 1H, J=6.4 and 7.5 Hz, H-1'), 5.31 (d, 1H, $D_2O$ exchangeable, 3'-OH), 5.19 (t, 1H, $D_2O$ exchangeable, 5'-OH), 4.70 (br s, 2H, Ph-$CH_2$), 4.41 (m, 1H, H-3'), 4.26 (d, 2H, J=4.3 Hz, $CH_2$) 3.88 (m, 1H, H-4'), 3.61 (m, 1H, H-5'a), 3.53 (m, 1H, H-5'b), 2.73 (m, 1H, H-2'a), 2.25 (m, 1H, H-2'b).

$N^6$-[4-(3-Amino-1-propyl)benzyl]-2'-deoxyadenosine-5'-triphosphate (dA.n8)

$POCl_3$ (16 µL, 0.17 mmol) was added to a solution of compound dA.n7 (56 mg, 0.11 mmol) and proton sponge (37 mg, 0.17 mmol) in trimethylphosphate (0.5 mL) and maintained at minus 20-30° C. for two hours. A solution of bis-tri-n-butylammonium pyrophosphate (261 mg, 0.55 mmol) and tri-n-butylamine (110 µL) in anhydrous DMF (1.1 mL) was added. After five minutes of stirring, triethylammonium bicarbonate buffer (1 M, pH 7.5; 10 mL) was added. The reaction was stirred for one hour at room temperature, followed by the dropwise addition of concentrated ammonium hydroxide (10 mL, 27%) at 0° C. The mixture was stirred for an additional hour at room temperature and then lyophilized to dryness. The residue obtained was dissolved in water (10 mL), filtered, and purified by anion exchange chromatography using a Q Sepharose FF column (2.5×20 cm) with a linear gradient of $NH_4HCO_3$ (50 mM to 500 mM in 300 minutes) at a flow rate of 4.5 mL/min. The fractions containing triphosphate were combined and lyophilized to give triphosphate dA.n8 (63 mg, 84%) as a white fluffy solid.

$^1$H NMR (400 MHz, $D_2O$): δ 8.41 (s, 1H, H-8), 8.19 (s, 1H, H-2), 7.38-7.26 (m, 4H, Ph-H), 6.47 (dd, 1H, J=5.5 and 6.6 Hz, H-1'), 4.30 (s, 1H, H-4'), 4.21 (m, 2H, H-5'a and H-5'b), 3.63 (s, 2H, $CH_2$), 2.79 (m, 1H, H-2'a), 2.60 (m, 1H, H-2'b).

$^{31}$P NMR (162 MHz, $D_2O$): δ −5.80 (d, J=20.1 Hz), −10.94 (d, J=19.3 Hz), −21.59 (t, J=19.3 Hz);

ToF-MS (ESI): For the molecular ion $C_{20}H_{23}N_6O_{12}P_3Na$ [M−2H+Na]$^-$, the calculated mass was 655.0485, and the observed mass was 655.0758.

6-FAM labeled $N^6$-[4-(3-Amino-1-propyl)benzyl]-2'-deoxyadenosine-5'-triphosphate (WW2p085)

A solution of 6-FAM-SE (3.5 mg, 7.35 µmol) in anhydrous DMSO (70 µL) was added to a solution of triphosphate dA.18a (3.5 µmol) in $Na_2CO_3$/$NaHCO_3$ buffer (0.1 M, pH 9.2; 600 µL) and incubated at room temperature for one hour. The reaction was purified by reverse-phase HPLC using a Perkin Elmer OD-300 $C_{18}$ column (4.6×250 mm) to yield the 6-FAM labeled triphosphate WW2p085. Mobile phase: A, 100 mM triethylammonium acetate (TEAA) in water (pH 7.0); B, 100 mM TEAA in water/$CH_3CN$ (30:70). Elution was performed with a linear gradient of 5-20% B for 20 minutes and then 20-90% B for 20 minutes. The concentration of WW2p085 was estimated by adsorption spectroscopy using the extinction coefficient of the 6-FAM dye (i.e., 68,000 at 494 nm).

ToF-MS (ESI): For the molecular ion $C_{41}H_{36}N_6O_{18}P_3$ [M+H]$^+$, the calculated mass was 993.1299, and the observed mass was 993.1520.
Synthesis of 6-FAM labeled $N^6$-{1-[4-(3-amino-1-propynyl)phenyl]ethyl}-2'-deoxyadenosine triphosphate (WW2p093)
Scheme. Synthesis of 6-FAM labeled $N^6$-{1-[4-(3-amino-1-propynyl)phenyl]ethyl}-2'-deoxyadenosine triphosphate.
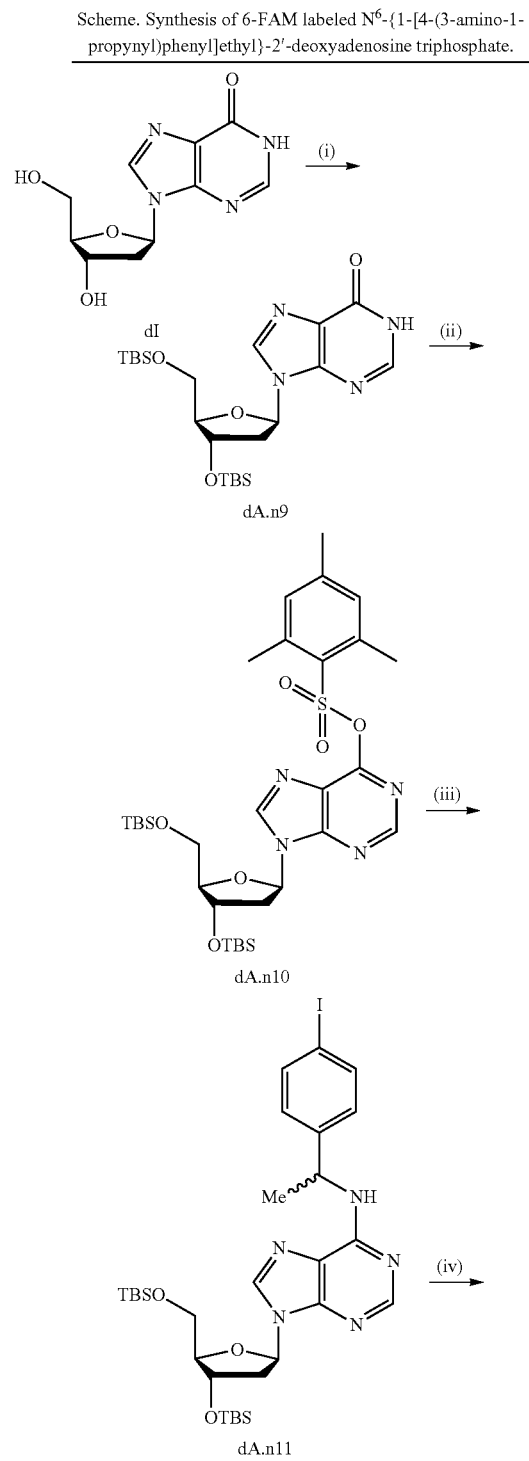
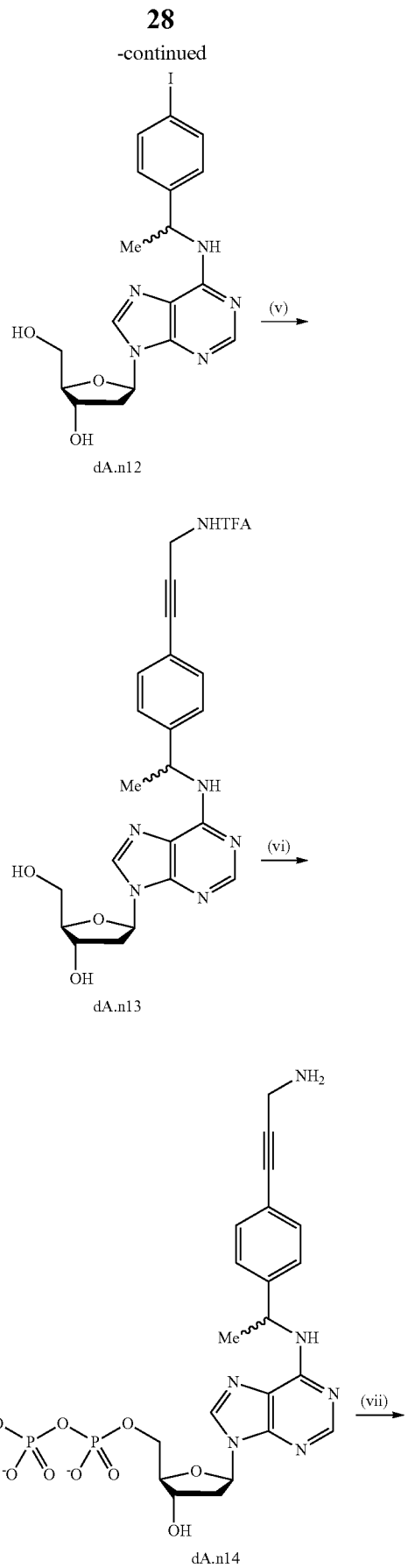

-continued

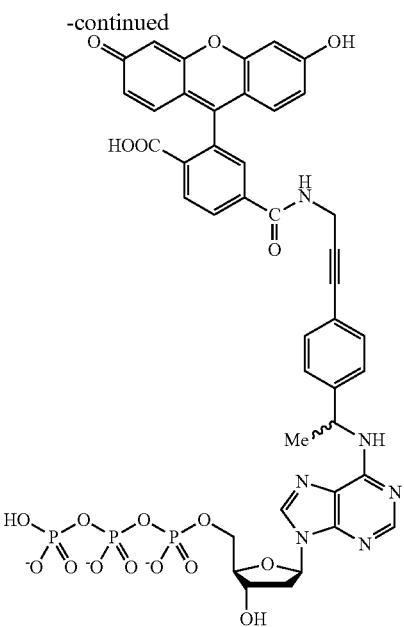

WW2p093

(i) TBSCl, imidazole, anhydrous DMF, 0° C., then gradually warmed to room temperature, 12 hours, 83%; (ii) 2-mesitylenesulfonyl chloride, Et₃N, DMAP, anhydrous CH₂Cl₂, room temperature, 1.5 hours, 20%; (iii) 1-(4-iodophenyl)ethylamine, molecular sieves, anhydrous 1,4-dioxane, 50° C., 18 hours, 88%; (iv) n-Bu₄NF, THF, 0° C., then gradually warmed to room temperature, 93%; (v) N-propargyltrifluoroacetamide, Pd(PPh₃)₄(0), CuI, Et₃N, anhydrous DMF, 4.5 hours, 86%; (vi) POCl₃, (MeO)₃PO, minus 20-30° C.; (n-Bu₃NH)₂H₂P₂O₇, n-Bu₃N, DMF; 1 M HNEt₃HCO₃; 86%

(vii) 6-FAM—SE, 0.1 M NaHCO₃/Na₂CO₃, pH 9.2, one hour.

3',5'-O-Bis-tert-butyldimethylsilyl-2'-deoxyinosine (dA.n9)[1]

[1] The exact procedure can be found in: Kiselyov, A. S.; Steinbrecher, T.; Harvey, R. G. (1995) "Synthesis of the Fjord-region cis- and trans-Amino Triol Derivatives of the carcinogenic Hydrocarbon Benzo[g]chrysene and Utilization for the Synthesis of a Deoxyadenosine Adduct Linked to the N6-Amino Group" *J. Org. Chem.*, 60: 6129-6134.

A solution of TBSCl (1.91 g, 12.67 mmol) was added to a solution of 2'-deoxyinosine (1.00 g, 3.96 mmol) and imidiazole (1.73 g, 25.34 mmol) in anhydrous DMF (3 mL) at 0° C. under nitrogen atmosphere. The reaction mixture was gradually warmed to room temperature and stirred for 12 hours. The mixture was then concentrated in vacuo, dissolved in CH₂Cl₂ (100 mL), washed twice with water (50 mL), dried over anhydrous Na₂SO₄, concentrated in vacuo, and purified by silica gel chromatography to yield 3',5'-O-bis-tert-butyldimethylsilyl-2'-deoxyinosine dA.n9 (1.58 g, 83%) as a white powder.

$^1$H NMR (400 MHz, DMSO-d₆): δ 12.37 (br s, 1H, D₂O exchangeable, NH), 8.25 (s, 1H, H-8), 8.04 (d, 1H, J=3.6 Hz, H-2), 6.29 (t, 1H, J=6.6 Hz, H-1'), 4.59 (m, 1H, H-3'), 3.84 (m, 1H, H-4'), 3.74 (m, 1H, H-5'a), 3.66 (m, 1H, H-5'b), 2.76 (m, 1H, H-2'a), 2.30 (m, 1H, H-2'b), 0.89 (s, 9H, (CH₃)₃CSi), 0.85 (s, 9H, (CH₃)₃CSi), 0.11 (s, 6H, (CH₃)₂Si), 0.02 (2 s, 6H, (CH₃)₂Si).

O⁶-(2-Mesitylenesulfonyl)-3',5'-bis-O-tert-butyldimethylsilyl-2'-deoxyinosine (dA.n10)[1]

2-Mesitylenesulfonyl chloride (0.70 g, 2.12 mmol), Et₃N (0.42 mL, 3.07 mmol), and DMAP (16 mg, 0.13 mmol) were added to a solution of dA.n9 (1.02 g, 2.12 mmol) in anhydrous CH₂Cl₂ (15 mL). The reaction mixture was stirred at room temperature for 1.5 hours, then diluted with ethyl ether (50 mL). The ether solution was washed twice with a saturated solution of NaHCO₃ (25 mL each) and then with brine (25 mL). The organic layer was dried over Na₂SO₄, concentrated in vacuo, and purified by silica gel chromatography to yield O⁶-(2-mesitylenesulfonyl)-3',5'-bis-O-tert-butyldimethylsilyl-2'-deoxyinosine dA.n10 (279 mg, 20%).

$^1$H NMR (400 MHz, CDCl₃): δ 8.55 (s, 1H, H-8), 8.38 (s, 1H, H-2), 6.99 (s, 2H, Ph-H), 6.48 (t, 1H, J=6.4 Hz, H-1'), 4.61 (m, 1H, H-3'), 4.03 (m, 1H, H-4'), 3.85 (m, 1H, H-5'a), 3.76 (m, 1H, H-5'b), 2.77 (s, 6H, CH₃), 2.61 (m, 1H, H-2'a), 2.43 (m, 1H, H-2'b), 2.32 (s, 3H, CH₃), 0.91 (s, 9H, (CH₃)₃CSi), 0.89 (s, 9H, (CH₃)₃CSi), 0.09 (s, 6H, (CH₃)₂Si), 0.08 (2 s, 6H, (CH₃)₂Si).

N⁶-[1-(4-Iodophenyl)ethyl]-3',5'-bis-O-tert-butyldimethylsilyl-2'-deoxyadenosine (dA.n11)

A solution of 1-(4-iodophenyl)ethylamine (312 mg, 1.26 mmol) in anhydrous 1,4-dioxane (1 mL) was added to a solution of dA.n10 (279 mg, 0.42 mmol) in anhydrous 1,4-dioxane (2 mL) containing molecular sieves (4 Å, 8-12 Mesh, 0.75 g) at room temperature under nitrogen atmosphere. The mixture was then stirred at 50° C. for 18 hours. The solvent was removed in vacuo, and the crude product was purified by silica gel column chromatography to yield N⁶-[1-(4-iodophenyl)ethyl]-3',5'-bis-O-tert-butyldimethylsilyl-2'-deoxyadenosine dA.n11 (263 mg, 88%, 1:1 mixture of diastereoisomers) as a white foam.

$^1$H NMR (400 MHz, CDCl₃) for diastereoisomers: δ 8.32 (s, 1H, H-8), 8.08 (s, 1H, H-2), 7.61 (m, 2H, Ph-H), 7.15 (m, 2H, Ph-H), 6.42 (t, 1H, J=6.4 Hz, H-1'), 6.20 (br m, 1H, NH), 5.50 (br s, 1H, Ph-CH), 4.59 (m, 1H, H-3'), 3.99 (m, 1H, H-4'), 3.85 (m, 1H, H-5'a), 3.77 (m, 1H, H-5'b), 2.60 (m, 1H, H-2'a), 2.42 (m, 1H, H-2'b), 1.59 (d, 3H, J=7.0 Hz, CH₃), 0.90 (s, 18H, (CH₃)₃CSi), 0.08 (s, 12H, (CH₃)₂Si);

$^{13}$C NMR (100 MHz, MeOH-d₄) for diastereoisomers: δ 153.78 (C), 151.94 (CH), 143.78/143.71 (C), 138.36 (CH), 137.57 (CH), 128.17/128.16 (CH), 119.99 (C), 92.41 (C), 87.81/87.79 (CH), 84.28 (CH), 71.78/71.74 (CH), 62.72/62.68 (CH₂), 49.40 (br, CH), 41.31 (CH₂), 25.96 (CH₃), 25.75 (CH₃), 22.64 (CH₃), 18.41 (C), 17.99 (C), −4.66 (CH₃), −4.82 (CH₃), −5.39 (CH₃), −5.48 (CH₃).

N⁶-[1-(4-Iodophenyl)ethyl]-2'-deoxyadenosine (dA.n12)

A solution of n-Bu₄NF (409 mg, 1.30 mmol) in THF (3 mL) was added to a solution of compound dA.n11 (263 mg, 0.37 mmol) in THF (5 mL) at 0° C. The reaction mixture was gradually warmed to room temperature and stirred for 30 minutes, then concentrated in vacuo to dryness. The residue was purified by silica gel column chromatography to yield N⁶-[1-(4-iodophenyl)ethyl]-2'-deoxyadenosine dA.n12 (164 mg, 93% 1:1 mixture of diastereoisomers) as a waxy solid.

$^1$H NMR (400 MHz, DMSO-d₆) for diastereomers: δ 8.35 (s, 1H, H-8), 8.32 (br s, 1H, D₂O exchangeable, NH), 8.13 (s, 1H, H-2), 7.62 (d, 2H, J=8.2 Hz, Ph-H), 7.22 (d, 2H, 2H, J=8.2 Hz, Ph-H), 6.32 (m, 1H, H-1'), 5.41 (br, 1H, Ph-CH), 5.31 (d, 1H, D₂O exchangeable, 3'-OH), 5.19 (m, 1H, D₂O exchangeable, 5'-OH), 4.35 (m, 1H, H-4'), 3.85 (m, 1H, H-4'), 3.58 (m, 1H, H-5'a), 3.48 (m, 1H, H-5'b), 2.68 (m, 1H, H-2'a), 2.22 (m, 1H, H-2'b), 1.49 (d, 3H, J=7.0 Hz, CH₃).

N⁶-{1-[4-(3-Trifluoroacetamido-1-propynyl)phenyl]ethyl}-2'-deoxyadenosine (dA.n13)

A solution of compound dA.n12 (70 mg, 0.145 mmol), N-propargyltrifluoroacetamide (66 mg, 0.44 mmol), CuI (5.5 mg, 0.03 mmol), tetrakis(triphenylphosphine)-palladium(0) (17 mg, 0.015 mmol), and Et$_3$N (41 μL, 0.29 mmol) in anhydrous DMF (2.2 mL) was stirred at room temperature for 5.5 hours. The mixture was concentrated in vacuo and purified by silica gel column chromatography to yield N$^6$-{1-[4-(3-trifluoroacetamido-1-propynyl)phenyl]ethyl}-2'-deoxyadenosine dA.n13 (63 mg, 86%, 1:1 mixture of diastereoisomers) as a waxy solid.

$^1$H NMR (400 MHz, DMSO-d$_6$) for diastereomers: δ 10.05 (t, 1H, J=5.4 Hz, D$_2$O exchangeable, NH), 8.36 (s, 1H, H-8), 8.34 (br s, 1H, D$_2$O exchangeable, NH), 8.15 (s, 1H, H-2), 7.43 (d, 2H, J=8.2 Hz, Ph-H), 7.36 (d, 2H, 2H, J=8.2 Hz, Ph-H), 6.33 (dd, 1H, J=6.4 and 7.5, Hz, H-1'), 5.49 (br, 1H, Ph-CH), 5.30 (d, 1H, D$_2$O exchangeable, 3'-OH), 5.10 (m, 1H, D$_2$O exchangeable, 5'-OH), 4.39 (m, 1H, H-3'), 4.25 (d, 2H, J=5.4 Hz, CH$_2$), 3.87 (m, 1H, H-3'), 3.59 (m, 1H, H-5'a), 3.51 (m, 1H, H-5'b), 2.72 (m, 1H, H-2'a), 2.24 (m, 1H, H-2'b), 1.52 (d, 3H, J=7.0 Hz, CH$_3$);

N$^6$-{1-[4-(3-Amino-1-propynyl)phenyl]ethyl}-2'-deoxyadenosine-5'-triphosphate (dA.n14)

POCl$_3$ (14 μL, 0.15 mmol) was added to a solution of compound dA.n14 (51 mg, 0.1 mmol) and proton sponge (32 mg, 0.15 mmol) in trimethylphosphate (0.5 mL) and maintained at minus 20-30° C. for two hours. A solution of bis-tri-n-butylammonium pyrophosphate (237 mg, 0.5 mmol) and tri-n-butylamine (100 μL) in anhydrous DMF (1.0 mL) was added. After five minutes of stirring, triethylammonium bicarbonate buffer (1 M, pH 7.5; 10 mL) was added. The reaction was stirred for one hour at room temperature, followed by the dropwise addition of concentrated ammonium hydroxide (10 mL, 27%) at 0° C. The mixture was stirred for an additional hour at room temperature and then lyophilized to dryness. The residue obtained was dissolved in water (10 mL), filtered, and purified by anion exchange chromatography using a Q Sepharose FF column (2.5×20 cm) with a linear gradient of NH$_4$HCO$_3$ (50 mM to 500 mM in 300 minutes) at a flow rate of 4.5 mL/min. The fractions containing triphosphate were combined and lyophilized to give triphosphate dA.n14 (60 mg, 86%, 1:1 mixture of diastereoisomers) as a white fluffy solid.

$^1$H NMR (400 MHz, D$_2$O) for diastereoisomers: δ 8.41 (s, 1H, H-8), 8.14 (2 s, 1H, H-2), 7.38 (m, 4H, Ph-H), 6.46 (m, 1H, H-1'), 5.32 (br, 1H, Ph-CH), 4.30 (s, 1H, H-3'), 4.20 (m, 2H, H-5'a and H-5'b), 3.61 (s, 2H, CH$_2$), 2.78 (m, 1H, H-2'a), 2.59 (m, 1H, H-2'b), 1.60 (d, 3H, J=6.9 Hz, CH$_3$);

$^{31}$P NMR (162 MHz, D$_2$O): δ −6.02 (d, J=19.4 Hz), −11.19 (d, J=19.4 Hz), −21.77 (t, J=19.4 Hz);

ToF-MS (ESI): For the molecular ion C$_{21}$H$_{25}$N$_6$O$_{12}$P$_3$Na [M−2H+Na]$^-$, the calculated mass was 669.0641, and the observed mass was 669.0960.

6-FAM labeled N$^6$-{1-[4-(3-Amino-1-propynyl)phenyl]ethyl}-2'-deoxyadenosine-5'-triphosphate (WW2p093)

A solution of 6-FAM-SE (3.5 mg, 7.4 μmol) in anhydrous DMSO (70 μL) was added to a solution of triphosphate dA.n14 (4.1 μmol) in Na$_2$CO$_3$/NaHCO$_3$ buffer (0.1 M, pH 9.2; 600 μL) and incubated at room temperature for one hour. The reaction was purified by reverse-phase HPLC using a Perkin Elmer OD-300 C$_{18}$ column (4.6×250 mm) to yield the 6-FAM labeled triphosphate WW2p093. Mobile phase: A, 100 mM triethylammonium acetate (TEAA) in water (pH 7.0); B, 100 mM TEAA in water/CH$_3$CN (30:70). HPLC purification was achieved using a linear gradient of 5-20% B for 20 minutes and then 20-90% B for 20 minutes. The concentration of WW2p093 was estimated by adsorption spectroscopy using the extinction coefficient of the 6-FAM dye (i.e., 68,000 at 494 nm).

All patents and patent publications referred to herein are hereby incorporated by reference. Certain modifications and improvements will occur to those skilled in the art upon a reading of the foregoing description. It should be understood that all such modifications and improvements have been deleted herein for the sake of conciseness and readability but are properly within the scope of the following claims.

What is claimed is:

1. A method of determining the sequence of a target nucleic acid comprising
   (i) adding a target nucleic acid to a Sanger or Sanger-type sequencing apparatus,
   (ii) adding one or more compounds of the formula:

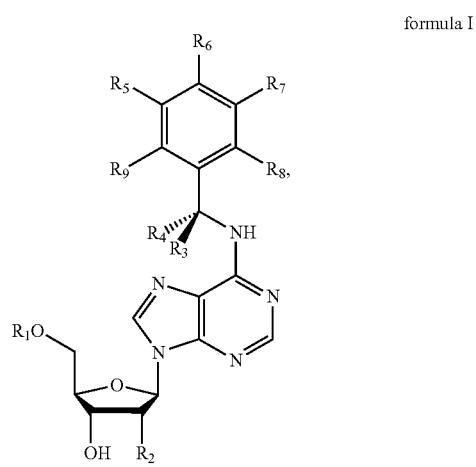

formula I

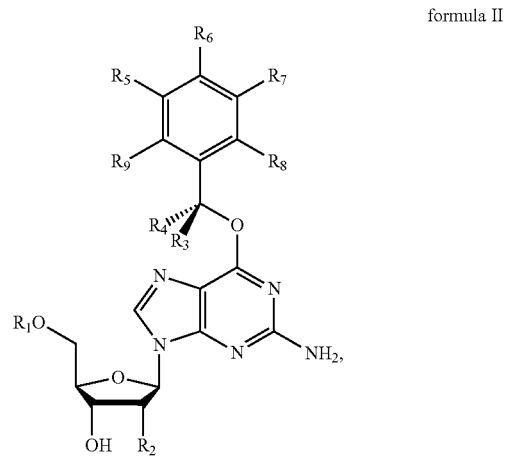

formula II formula III

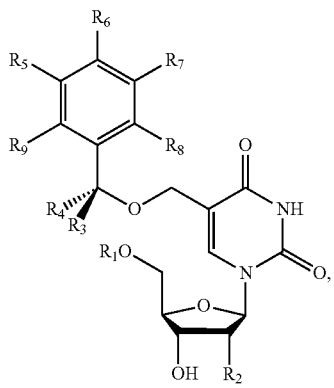

formula IV

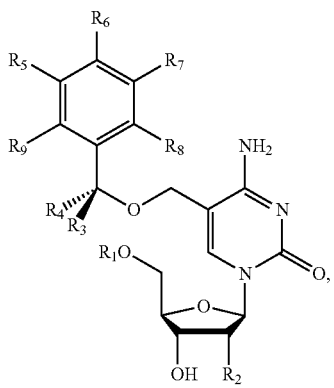

formula V

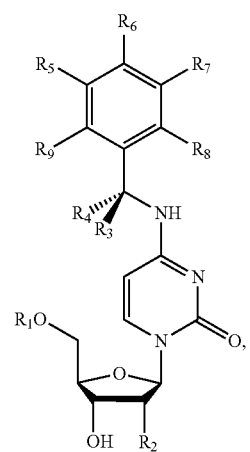

formula VI

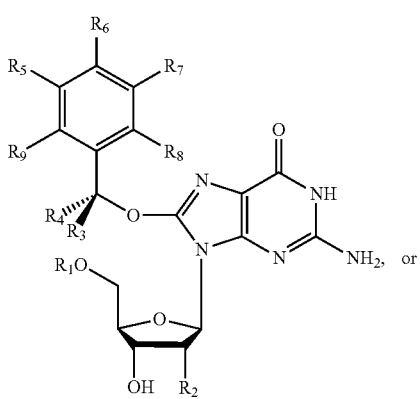

formula VII

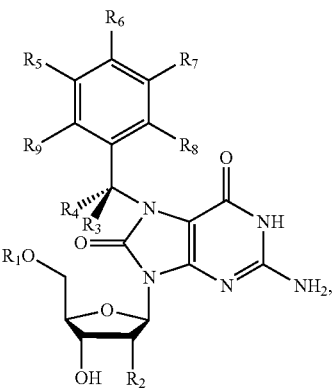

wherein $R_1$=H, monophosphate, diphosphate or triphosphate, $R_2$=H or OH, $R_3$ and $R_4$ are each independently selected from the group of H, a $C_1$-$C_{12}$ straight chain or branched alkyl, a $C_2$-$C_{12}$ straight chain or branched alkenyl or polyenyl, a $C_2$-$C_{12}$ straight chain or branched alkynyl or polyalkynyl, and an aromatic group, $R_5$, $R_6$, and $R_7$, are each independently selected from the group consisting of H, $OCH_3$, $NO_2$, CN, a halide, a $C_1$-$C_{12}$ straight chain or branched alkyl, a $C_2$-$C_{12}$ straight chain or branched alkenyl or polyenyl, a $C_2$-$C_{12}$ straight chain or branched alkynyl or polyalkynyl, and an aromatic group, with the proviso that one of $R_5$, $R_6$, and $R_7$ is a group of the structure:

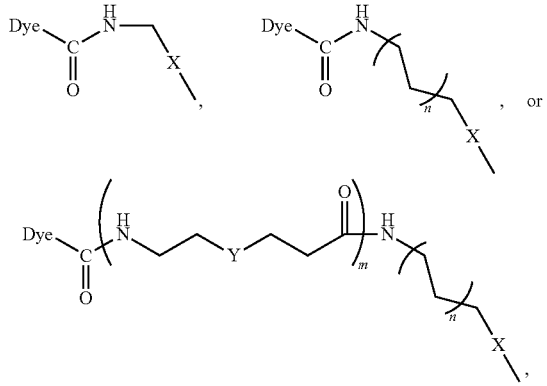

wherein X=$CH_2$, CH=CH, C≡C, O, S, or NH,
Y=$CH_2$, O, or NH,
n=an integer from 0-12;
m=an integer from 0-12, and
Dye=a fluorophore,
and $R_8$ and $R_9$ are as defined above for $R_5$, $R_6$, and $R_7$, with the proviso that neither $R_8$ nor $R_9$ is $NO_2$,
to the sequencing apparatus, with the proviso that where more than one type of base is present, each base is attached to a different fluorophore;

(iii) adding a complementary primer and a polymerase enzyme, (iv) performing a polymerase reaction to incorporate at least one of the compounds of step (ii) into a growing nucleic acid strand, and (v) analyzing the result of the Sanger sequencing reaction with fluorescence sequencing instrumentation or by pulsed multiline excitation fluorescence, wherein steps (i)-(iii) can be performed in any order.

2. The method according to claim 1, wherein incorporation of at least one compound according to step (iv) is followed by termination of strand growth at an efficiency of from about 90% to about 100%.

3. The method according to claim 1, wherein the incorporation of at least one compound according to step (iv) occurs at about 70% to about 100% of the efficiency of incorporation of a native substrate with the same base in the polymerase reaction.

4. The method according to claim 3, wherein the incorporation efficiency occurs at about 85% to about 100%.

5. The method according to claim 1, wherein the polymerase is selected from the group consisting of reverse transcriptase, terminal transferase, and DNA polymerase.

6. A method of incorporating a non-naturally occurring component into a nucleic acid comprising:

(i) adding a target nucleic acid to a sequencing apparatus;

(ii) adding one or more compounds of the formula:

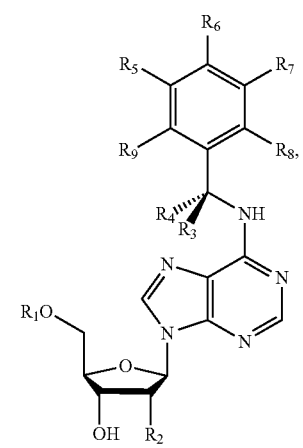

formula I

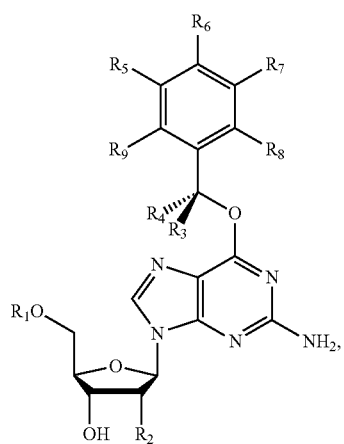

formula II

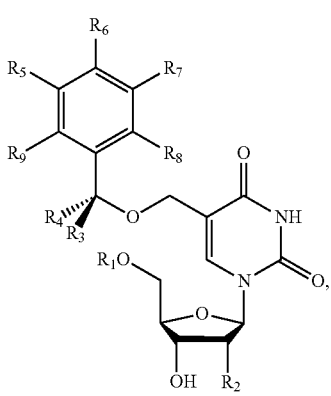

formula III

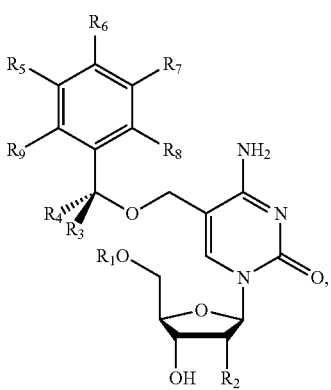

formula IV

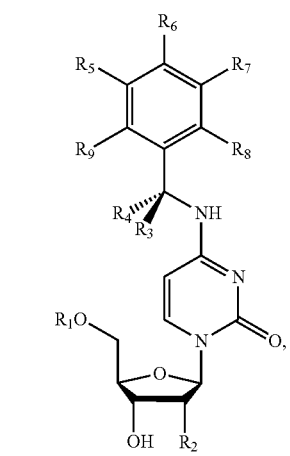

formula V

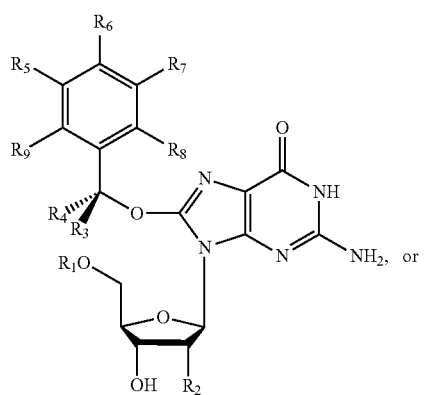

formula VI

-continued

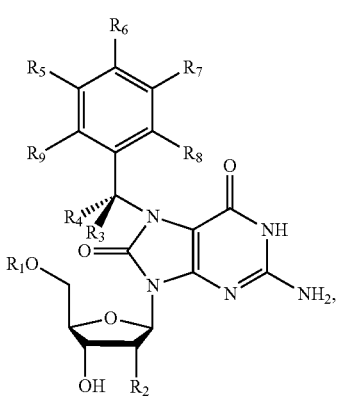

formula VII wherein $R_1$=H, monophosphate, diphosphate or triphosphate, $R_2$=H or OH, $R_3$ and $R_4$ are each independently selected from the group of H, a $C_1$-$C_{12}$ straight chain or branched alkyl, a $C_2$-$C_{12}$ straight chain or branched alkenyl or polyenyl, a $C_2$-$C_{12}$ straight chain or branched alkynyl or polyalkynyl, and an aromatic group, $R_5$, $R_6$, and $R_7$, are each independently selected from the group consisting of H, $OCH_3$, $NO_2$, CN, a halide, a $C_1$-$C_{12}$ straight chain or branched alkyl, a $C_2$-$C_{12}$ straight chain or branched alkenyl or polyenyl, a $C_2$-$C_{12}$ straight chain or branched alkynyl or polyalkynyl, and an aromatic group, with the proviso that one of $R_5$, $R_6$, and $R_7$ is a group of the structure:

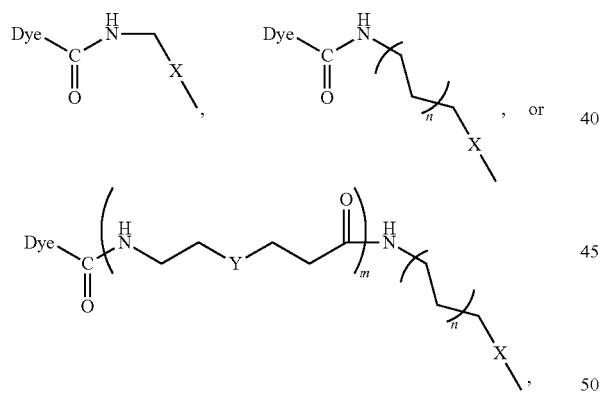

wherein X=$CH_2$, CH=CH, C≡C, O, S, or NH,
Y=$CH_2$, O, or NH,
n=an integer from 0-12;
m=an integer from 0-12, and
Dye=a fluorophore,
and $R_8$ and $R_9$ are as defined above for $R_5$, $R_6$, and $R_7$, with the proviso that neither $R_8$ nor $R_9$ is $NO_2$,
to the sequencing apparatus, with the proviso that where more than one type of base is present, each base is attached to a different fluorophore;

(iii) adding a polymerase enzyme; and
(iv) performing a polymerase reaction to incorporate at least one of the compounds of step (ii) into a growing nucleic acid strand,
wherein steps (i)-(iii) can be performed in any order.

7. The method according to claim 6, further comprising
(v) analyzing the result of the polymerase chain reaction for incorporation of at least one compound from step (ii).

8. The method according to claim 6, wherein incorporation of at least one compound according to step (iv) is followed by termination of strand growth at an efficiency of from about 90% to about 100%.

9. The method according to claim 6, wherein the incorporation of at least one compound according to step (iv) occurs at about 70% to about 100% of the efficiency of incorporation of native substrate with the same base in the polymerase reaction a native substrate with the same base in the polymerase reaction.

10. A method of terminating nucleic acid synthesis comprising the step of placing a compound of the formula:

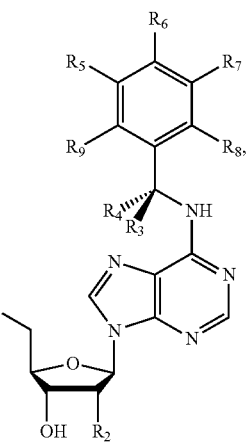

formula I

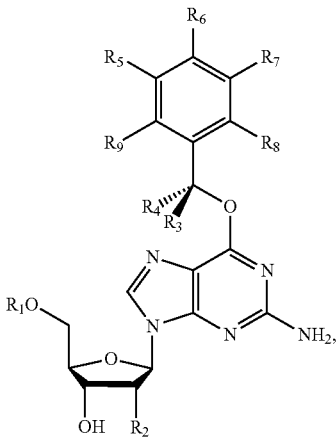

formula II

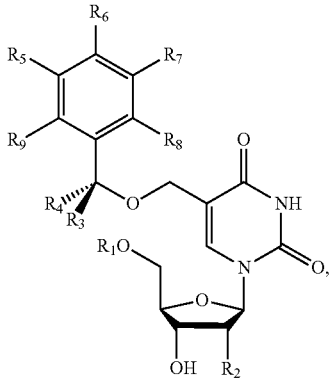

formula III

-continued formula IV

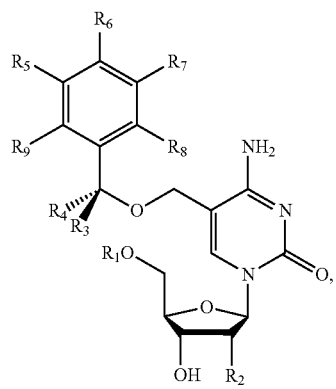

formula V

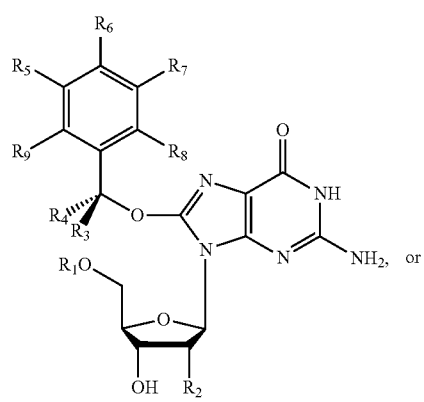

formula VI

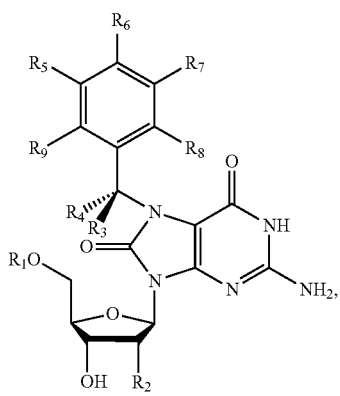

formula VII wherein $R_1$=H, monophosphate, diphosphate or triphosphate, $R_2$=H or OH, $R_3$ and $R_4$ are each independently selected from the group of H, a $C_1$-$C_{12}$ straight chain or branched alkyl, a $C_2$-$C_{12}$ straight chain or branched alkenyl or polyenyl, a $C_2$-$C_{12}$ straight chain or branched alkynyl or polyalkynyl, and an aromatic group, $R_5$, $R_6$, and $R_7$, are each independently selected from the group consisting of H, $OCH_3$, $NO_2$, CN, a halide, a $C_1$-$C_{12}$ straight chain or branched alkyl, a $C_2$-$C_{12}$ straight chain or branched alkenyl or polyenyl, a $C_2$-$C_{12}$ straight chain or branched alkynyl or polyalkynyl, and an aromatic group, with the proviso that one of $R_5$, $R_6$, and $R_7$ is a group of the structure:

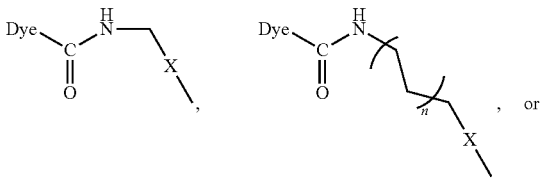

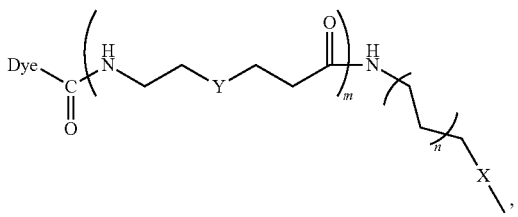

wherein X=$CH_2$, CH=CH, C≡C, O, S, or NH,

Y=$CH_2$, O, or NH, n=an integer from 0-12;

m=an integer from 0-12, and

Dye=a fluorophore, and $R_8$ and $R_9$ are as defined above for $R_5$, $R_6$, and $R_7$, with the proviso that neither $R_8$ nor $R_9$ is $NO_2$, in the environment of a polymerase and allowing incorporation of the compound into a nucleic acid.

11. The method according to claim 10 wherein the efficiency of termination upon incorporation of the compound ranges from about 90% to about 100%.

12. The method according to claim 10 wherein the efficiency of incorporation of the compound ranges from about 70% to about 100% compared to the efficiency of incorporation of a naturally-occurring nucleotide or nucleoside with the same base.

13. A method of performing Sanger or Sanger-type sequencing comprising addition of a compound of the formula:

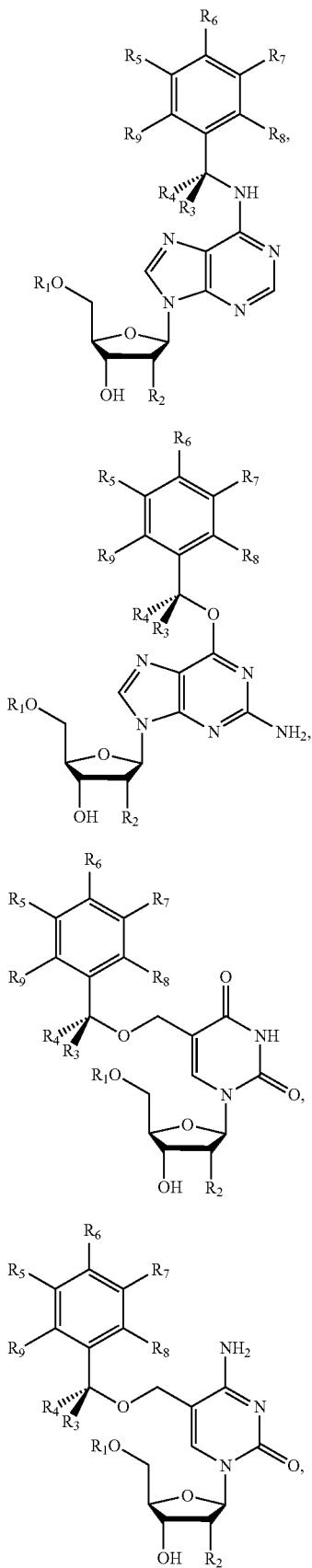

formula I formula II formula III formula IV

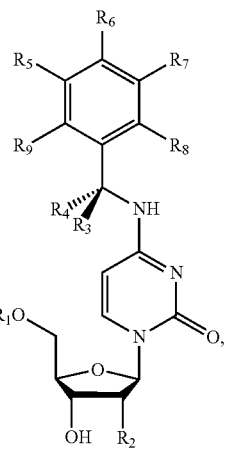

formula V

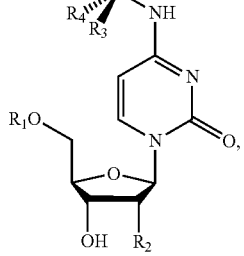

formula VI

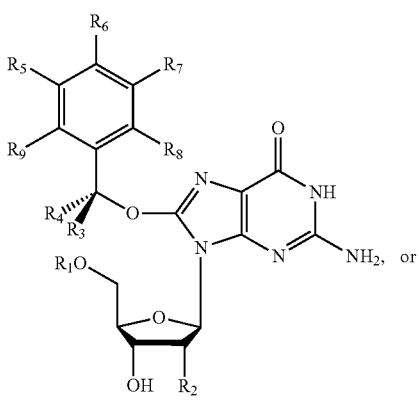

formula VII

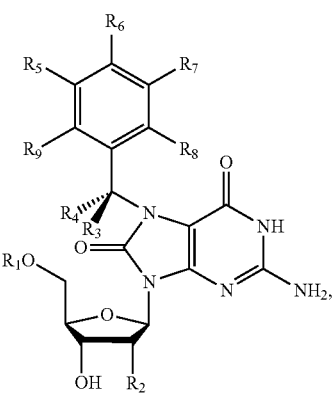

wherein $R_1$=H, monophosphate, diphosphate or triphosphate, $R_2$=H or OH, $R_3$ and $R_4$ are each independently selected from the group of H, a $C_1$-$C_{12}$ straight chain or branched alkyl, a $C_2$-$C_{12}$ straight chain or branched alkenyl or polyenyl, a $C_2$-$C_{12}$ straight chain or branched alkynyl or polyalkynyl, and an aromatic group, $R_5$, $R_6$, and $R_7$, are each independently selected from the group consisting of H, $OCH_3$, $NO_2$, CN, a halide, a $C_1$-$C_{12}$ straight chain or branched alkyl, a $C_2$-$C_{12}$ straight chain or branched alkenyl or polyenyl, a $C_2$-$C_{12}$ straight chain or branched alkynyl or polyalkynyl, and an aromatic group, with the proviso that one of $R_5$, $R_6$, and $R_7$ is a group of the structure:

43

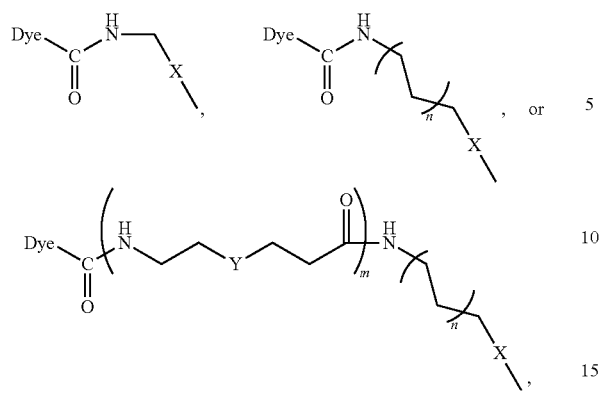, or

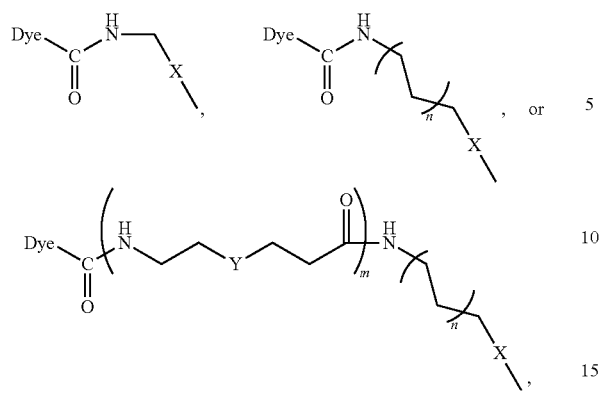

wherein X=CH$_2$, CH=CH, C≡C, O, S, or NH,
Y=CH$_2$, O, or NH,
n=an integer from 0-12;
m=an integer from 0-12, and
Dye=a fluorophore,
and R$_8$ and R$_9$ are as defined above for R$_5$, R$_6$, and R$_7$, with the proviso that neither R$_8$ nor R$_9$ is NO$_2$,
to a Sanger or Sanger-type sequencing method.

14. A method of performing mini-sequencing or minisequencing-type sequencing comprising addition of a compound of the formula:

formula I

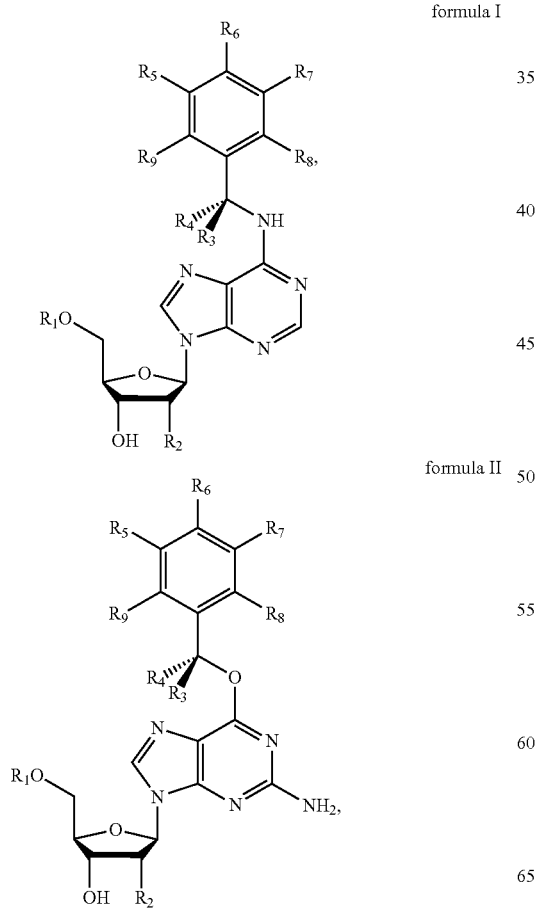

formula II formula III

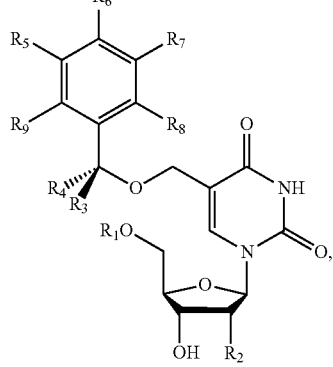

formula IV

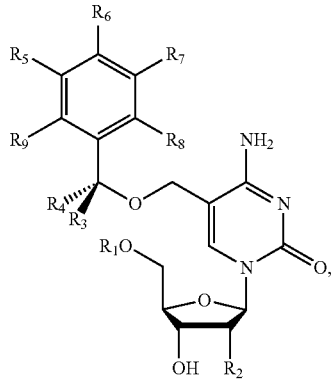

formula V formula VI

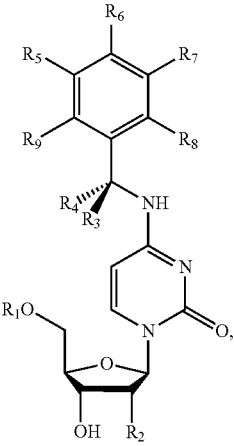

-continued formula VII

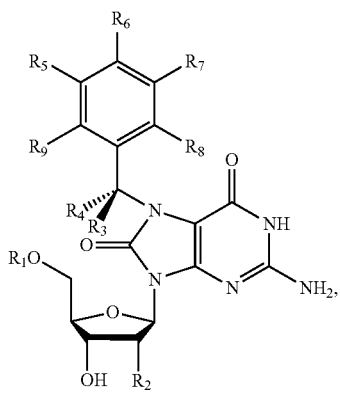

wherein $R_1$=H, monophosphate, diphosphate or triphosphate, $R_2$=H or OH, $R_3$ and $R_4$ are each independently selected from the group of H, a $C_1$-$C_{12}$ straight chain or branched alkyl, a $C_2$-$C_{12}$ straight chain or branched alkenyl or polyenyl, a $C_2$-$C_{12}$ straight chain or branched alkynyl or polyalkynyl, and an aromatic group, $R_5$, $R_6$, and $R_7$, are each independently selected from the group consisting of H, $OCH_3$, $NO_2$, CN, a halide, a $C_1$-$C_{12}$ straight chain or branched alkyl, a $C_2$-$C_{12}$ straight chain or branched alkenyl or polyenyl, a $C_2$-$C_{12}$ straight chain or branched alkynyl or polyalkynyl, and an aromatic group, with the proviso that one of $R_5$, $R_6$, and $R_7$ is a group of the structure:

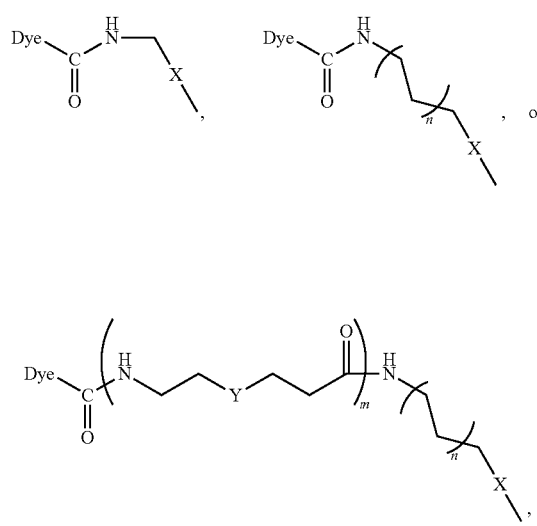

wherein X=$CH_2$, CH=CH, C≡C, O, S, or NH,

Y=$CH_2$, O, or NH, n=an integer from 0-12;

m=an integer from 0-12, and

Dye=a fluorophore, and $R_8$ and $R_9$ are as defined above for $R_5$, $R_6$, and $R_7$, with the proviso that neither $R_8$ nor $R_9$ is $NO_2$, to a mini-sequencing or minisequencing-type sequencing method.

15. The method according to any one of claims 1, 6, 10, 13, and 14, wherein $R_3$ and $R_4$ are each independently selected from the group consisting of H, —$CH_3$, —$CH_2CH_3$, —$CH_2CH_2CH_3$, isopropyl, tert-butyl and phenyl.

16. The method according to any one of claims 1, 6, 10, 13, and 14, wherein $R_3$ or $R_4$ are each independently selected from the group consisting of H, alkyl and aromatic groups optionally containing at least one heteroatom in the alkyl or aromatic groups, and further wherein the aromatic group may optionally be an aryl or polycyclic group.

17. The method of claim 16, wherein $R_3$ or $R_4$ is —$CH_3$ or isopropyl.

18. The method according to any one of claims 1, 6, 10, 13, and 14, wherein the compound is further defined as:

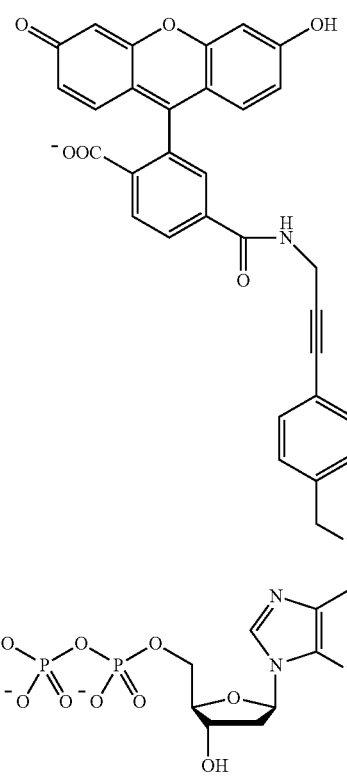

19. The method according to any one of claims 1, 6, 10, 13, and 14, wherein the compound is further defined as:

20. The method according to any one of claims 1, 6, 10, 13, and 14, wherein the compound is further defined as:
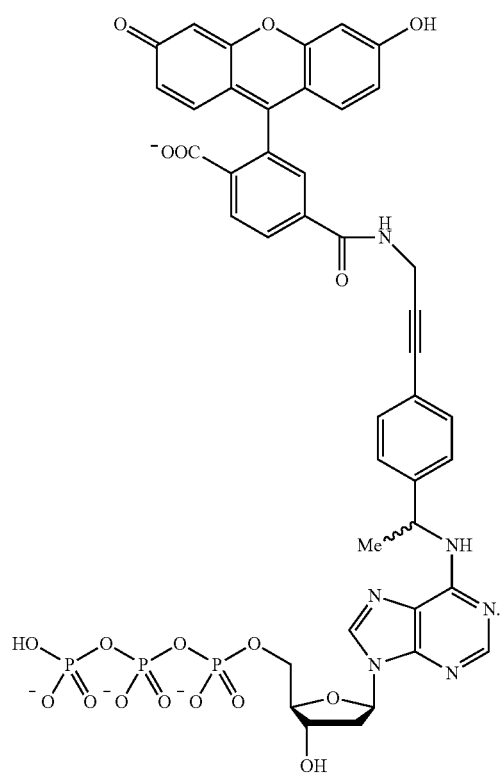
21. The method according to any one of claims 1, 6, 10, 13, and 14, wherein the compound is further defined as:
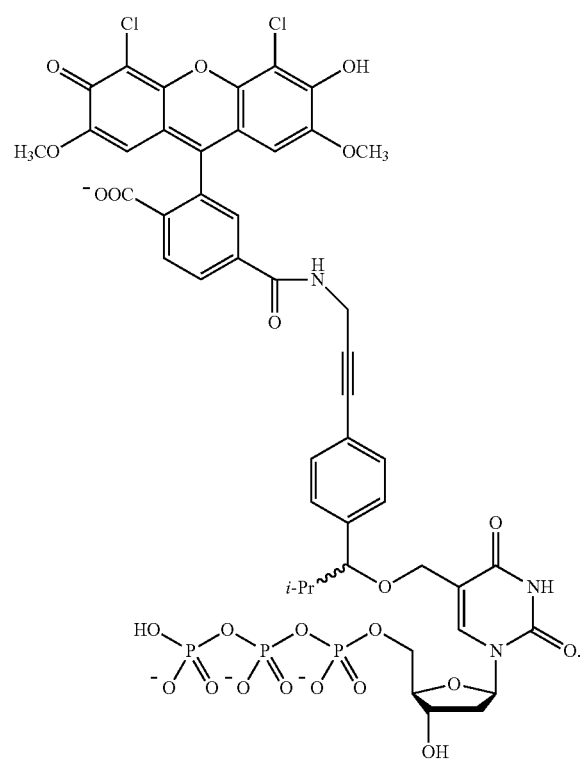
22. The method according to any one of claims 1, 6, 10, 13, and 14, wherein the compound is further defined as:
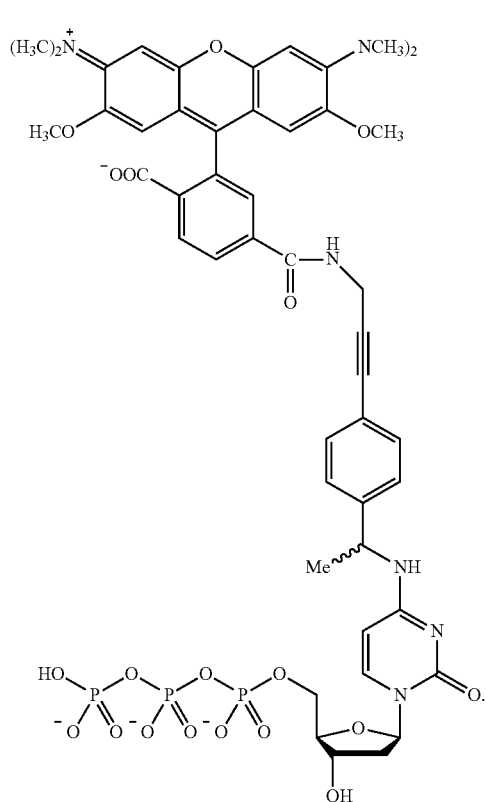
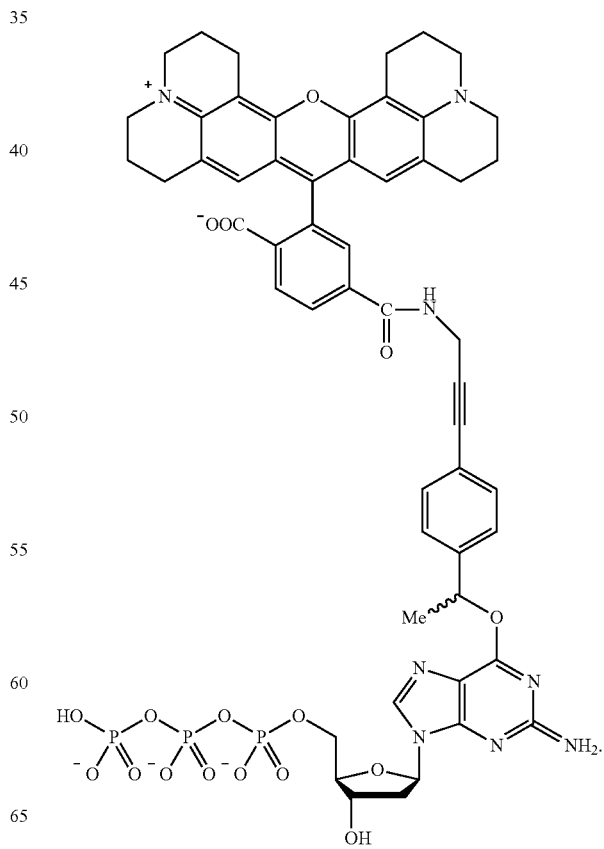

23. The method according to any one of claims 1, 6, 10, 13, and 14, wherein the compound is further defined as a compound of formula (I).

24. The method according to any one of claims 1, 6, 10, 13, and 14, wherein the compound is further defined as a compound of formula (II).

25. The method according to any one of claims 1, 6, 10, 13, and 14, wherein the compound is further defined as a compound of formula (III).

26. The method according to any one of claims 1, 6, 10, 13, and 14, wherein the compound is further defined as a compound of formula (IV).

27. The method according to any one of claims 1, 6, 10, 13, and 14, wherein the compound is further defined as a compound of formula (V).

28. The method according to any one of claims 1, 6, 10, 13, and 14, wherein the compound is further defined as a compound of formula (VI).

29. The method according to any one of claims 1, 6, 10, 13, and 14, wherein the compound is further defined as a compound of formula (VII).

* * * * *

UNITED STATES PATENT AND TRADEMARK OFFICE
CERTIFICATE OF CORRECTION

PATENT NO. : 8,198,029 B2
APPLICATION NO. : 12/986810
DATED : June 12, 2012
INVENTOR(S) : Weidong Wu et al.

It is certified that error appears in the above-identified patent and that said Letters Patent is hereby corrected as shown below:

In the Claims:

In claim 21, column 48, lines 1-31, delete the entire contents of lines 1-31 and insert

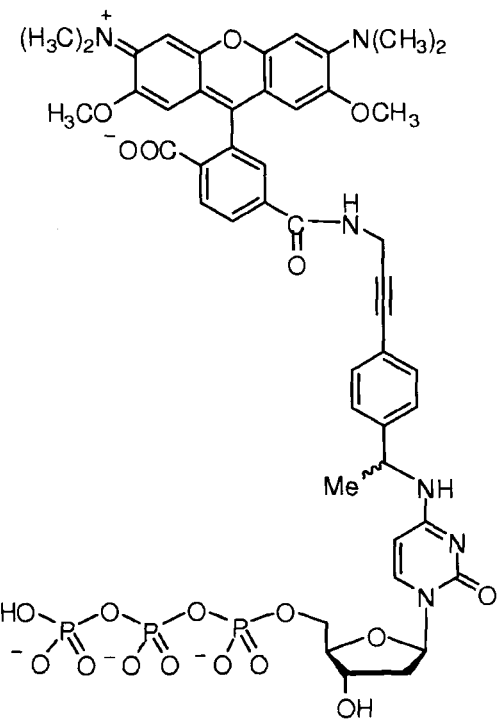

--, therefore.

Signed and Sealed this
Seventeenth Day of September, 2013

Teresa Stanek Rea
*Deputy Director of the United States Patent and Trademark Office*

CERTIFICATE OF CORRECTION (continued)
U.S. Pat. No. 8,198,029 B2

In claim 22, column 48, lines 35-66, delete the entire contents of lines 35-66 and insert

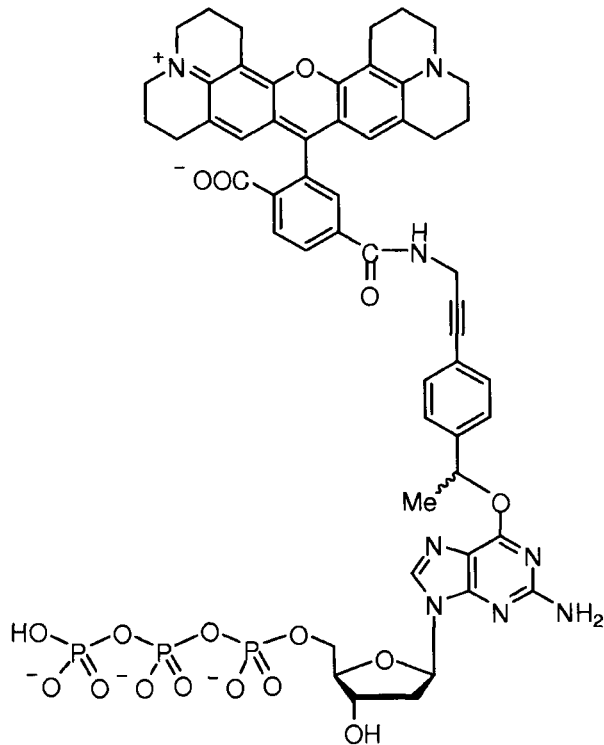

-- --, therefore.